(12) United States Patent
Wang et al.

(10) Patent No.: US 10,973,748 B2
(45) Date of Patent: Apr. 13, 2021

(54) COMPOSITIONS AND METHODS FOR LIGHTENING SKIN AND REDUCING HYPERPIGMENTATION

(71) Applicant: Versitech Limited, Hong Kong (HK)

(72) Inventors: Mingfu Wang, Hong Kong (HK); Shu Ting Hu, Kennedy Town (HK); Yi Zhen Wu, Kowloon (HK)

(73) Assignee: VERSITECH LIMITED, Hong Kong (HK)

( * ) Notice: Subject to any disclaimer, the term of this patent is extended or adjusted under 35 U.S.C. 154(b) by 0 days.

(21) Appl. No.: 16/095,616

(22) PCT Filed: Apr. 21, 2016

(86) PCT No.: PCT/CN2016/079834
§ 371 (c)(1),
(2) Date: Oct. 22, 2018

(87) PCT Pub. No.: WO2017/181379
PCT Pub. Date: Oct. 26, 2017

(65) Prior Publication Data
US 2019/0133907 A1    May 9, 2019

(51) Int. Cl.
| | | |
|---|---|---|
| *A61K 8/49* | (2006.01) |
| *A61K 45/06* | (2006.01) |
| *A61K 31/352* | (2006.01) |
| *C07D 311/30* | (2006.01) |
| *C07D 311/32* | (2006.01) |
| *A61P 17/00* | (2006.01) |
| *A61K 31/353* | (2006.01) |
| *A61Q 19/02* | (2006.01) |
| *A61K 8/9794* | (2017.01) |
| *A61K 8/9789* | (2017.01) |
| *A61K 8/44* | (2006.01) |

(52) U.S. Cl.
CPC ............ *A61K 8/498* (2013.01); *A61K 31/352* (2013.01); *A61K 31/353* (2013.01); *A61K 45/06* (2013.01); *A61P 17/00* (2018.01); *A61Q 19/02* (2013.01); *C07D 311/30* (2013.01); *C07D 311/32* (2013.01); *A61K 8/445* (2013.01); *A61K 8/9789* (2017.08); *A61K 8/9794* (2017.08)

(58) Field of Classification Search
None
See application file for complete search history.

(56) References Cited

U.S. PATENT DOCUMENTS

| | | |
|---|---|---|
| 4,254,105 A | 3/1981 | Fukuda |
| 4,925,673 A | 5/1990 | Steiner |
| 4,960,764 A | 10/1990 | Figueroa, Jr. |
| 5,013,556 A | 5/1991 | Woodle |
| 5,605,894 A | 2/1997 | Blank |
| 5,681,852 A | 10/1997 | Bissett |

FOREIGN PATENT DOCUMENTS

| | | |
|---|---|---|
| CN | 103342687 | 10/2013 |
| CN | 104758191 | 7/2015 |
| WO | 1992000373 | 1/1992 |
| WO | 9701313 | 1/1997 |
| WO | 9739733 | 10/1997 |

OTHER PUBLICATIONS

Nguyen et al., Journal of Natural Products (2012), 75(11), pp. 1951-1955.*
Barbosa et al., "A simple and economical modification of the Masson-Fontana method for staining melanin granules and enterochromaffin cells." Stain technology 59(4):193-196 (1984).
Bessou-Touya, et al., "Chimeric human epidermal reconstructs to study the role of melanocytes and keratinocytes in pigmentation and photoprotection," Journal of Investigative Dermatology 111(6):1103-1108 (1998).
Boissy, "Melanosome transfer to and translocation in the keratinocyte," Experimental Dermatology, 12(s2): 5-12 (2003).
Bouzaiene , et al., "Effect of apigenin-7-glucoside, genkwanin and naringenin on tyrosinase activity and melanin synthesis in B16F10 melanoma cells," Life Sciences, 144:80-85 (2016).
Cheng , et al., "Trapping of phenylacetaldehyde as a key mechanism responsible for naringenin's inhibitory activity in mutagenic 2-amino-1-methyl-6-phenylimidazo[4,5-b]pyridine formation," Chem. Res. Toxicol., 21(10):2026-2034 (2008).
Engasser P, et al., "Cosmetics and dermatology: bleaching creams," Journal of the American Academy of Dermatology, 5(2):143-7 (1981).
Kameyama K, et al, "Inhibitory effect of magnesium L-ascorbyl-2-phophate (VC-PMG) on melanogenesis in vitro and in vivo", J. Am. Aca. Dermatol., 17:381-386 (1996).
Kim, et al., "Autophagy induced by resveratrol suppresses α-MSH-induced melanogenesis," Experimental Dermatology, 23(3):204-206 (2014).
Lam, et al., "Application of a combined sulphorhodamine B and melanin assay to the evaluation of Chinese medicines and their constituent compounds for hyperpigmentation treatment," J Ethnopharmacol, 132(1):274-279 (2010).
Li , et al., "6-C-(E-phenylethenyl)-naringenin suppresses colorectal cancer growth by inhibiting cyclooxygenase-1," Cancer Res, 74(1):243-252 (2014).

(Continued)

*Primary Examiner* — Brian J Davis
(74) *Attorney, Agent, or Firm* — Pabst Patent Group LLP

(57) ABSTRACT

The composition includes a cyclic, unsaturated compound, preferably a polyphenol derivative. It reduces the synthesis of melanin by inhibiting the activity and expression levels of tyrosinase and related proteins, thereby preventing and limiting the content and distribution of melanin in mammalian skin. It also induces autophagy of melanosome, thereby restricting the synthesis, storage and transfer of melanin from melanocyte to keratinocyte. The dual modes of action allow for the efficacy of the composition at low dosage without causing toxicity to lighten skin and treat disorders associated with hyperpigmentation.

20 Claims, 4 Drawing Sheets

(56) References Cited

OTHER PUBLICATIONS

Maeda K, et al., "Arbutin: mechanism of its depigmenting action in human melanocyte culture," J. Pharmacol Exp Ther, 276(2):765-769 (1996).

Majmudar G, et al, "An in vitro method for screening skin-whitening products", J. Cosmet. Sci., 49:361-367 (1998).

Mathiowitz et al., "Novel microcapsules for delivery systems," Reactive Polymers, 6(2-3):275-283 (1987).

Mathiowitz, et al., "Polyanhydride microspheres as drug carriers II. Microencapsulation microencapsulation", J. Appl. Polymer Sci., 35: 755-774 (1988).

Mathiowitz, "Polyanhydride microshperes as drug carriers I. Hot-Melt Misroencapsulation", J. Controlled Release, 5:13-22 (1987).

Mizushima N, et al., "How to interpret LC3 immunoblotting," Autophagy, 3(6): 542-545 (2007).

Murase D, et al., "Autophagy Has a Significant Role in Determining Skin Color by Regulating Melanosome Degradation in Keratinocytes," Journal of Investigative Dermatology, 133(10): 2416-2424 (2013).

Ohguchi K, et al., "Stimulation of melanogenesis by the citrus flavonoid naringenin in mouse B16 melanoma cells," Bioscience, Biotechnology, and Biochemistry, 70(6):1499-1501 (2006).

Slominski, et al., "Melanin pigmentation in mammalian skin and its hormonal regulation," Physiological Reviews, 84(4): 1155-1228 (2004).

Smith, et al., "Selective cytotoxicity of hydroquinone for melanocyte-derived cells is mediated by tyrosinase activity but independent of melanin content," Pigment Cell Res, 1(6):386-389 (1988).

Solano F., et al., "Hypopigmenting agents: an updated review on biological, chemical and clinical aspects," Pigment Cell Res, 19(6):550-571 (2006).

Sun Products Formulary, "Oil in water creams", Cosmetics & Toiletries, vol. 102, pp. 117-136 Mar. 1987.

Sun Products Formulary, "Sunblocks", Cosmetics & Toiletries, vol. 105, pp. 122-139 Dec. 1990.

Zang R, et al., "Microwell bioreactor system for cell-based high throughput proliferation and cytotoxicity assays," Process Biochemistry, 48(1):78-88 (2013).

Zheng, et al., "A phenylacetaldehyde-flavonoid adduct, 8-C-(E-phenylethenyl)-norartocarpetin, exhibits intrinsic apoptosis and MAPK pathways-related anticancer potential on HepG2, SMMC-7721 and QGY-7703," Food Chemistry, 197:1089-1091 (2015).

International Search Report for PCT application PCT/CN2016/079834 dated Feb. 3, 2017.

'Autophagy Signaling Pathway,' Overview [online]. Autophagy Research Resources, Cell Signaling Technology, 2019 [retrieved on Mar. 11, 2019]. Retrieved from the Internet: <URL:www.cellsignal.com/contents/science-cst-pathways/autophagy-research-resources/science-pathways-autophagy>.

Costin, et al., "Human skin pigmentation: melanocytes modulate skin color in response to stress," The FASEB Journal, 21(4):976-994 (2007).

Loth, In: Modern Pharmaceutics (vol. 7 of the Series Drugs and the Pharmaceutical Sciences), issued von G. S. Banker and C. T. Rhodes, Marcel Dekker, Inc., New York, N. Y. 1979. Arch. Pharm. (Weinheim) 313: 813-814 (1980).

* cited by examiner

COMPOSITIONS AND METHODS FOR LIGHTENING SKIN AND REDUCING HYPERPIGMENTATION

CROSS-REFERENCE TO RELATED APPLICATIONS

This application is a National Phase application under 35 U.S.C. 371 of PCT/CN2016/079834, filed Apr. 21, 2016, the disclosure of which is hereby incorporated herein by reference in its entirety.

FIELD OF THE INVENTION

The disclosed invention is generally in the field of skin care and specifically in the area of skin lightening and depigmentation.

BACKGROUND OF THE INVENTION

Formulations to lighten skin tone and/or reduce hyperpigmentation provides therapeutic and/or aesthetic benefits. It is generally desirable to eliminate or inhibit the development of irregular pigmentation including melasma (chloasma or localized discoloration), age spots (Lentigo senilis) or liver spots (associated with sun damage or aging sometimes appearing as raised spots or Seborrheic keratoses) and freckles (Lentigo aestiva). The excess accumulation of melanin causes hyperpigmentation, which is associated with a number of diseases or disorders including solar lentigines, melasma, freckles and post-inflammatory hyperpigmentation. In most East Asian cultures, traditional aesthetics prefer a light skin tone.

The skin pigmentation is related to the amount and type of melanin synthesized by the epidermal melanocytes and its transfer to the neighboring keratinocytes. Tyrosinase (TYR) is a key enzyme in melanin synthesis, which catalyzes hydroxylation of L-tyrosine to 3,4-dihydroxyphenylalanine and its subsequent oxidation to dopaquinone (Slominski A, et al., *Physiological Reviews*, 84(4): 1155-1228 (2004)). Dopaquinone is converted through dopachrome into an indole derivative via autoxidation, and the conjugation of dopaquinone with this indole derivative produces melanin. Once synthesized in the cell body of the epidermal melanocyte, pigmented melanosomes are translocated down the dendrites and captured at the dendritic tips via various cytoskeletal elements. When incorporated into the keratinocytes, melanosomes are distributed individually or as clusters, aggregated towards the apical pole of the nucleus. Ultraviolet irradiation (UVR) can modulate the process of melanosome transfer from the melanocytes to the keratinocytes. (Boissy R E, *Experimental Dermatology*, 12(s2): 5-12 (2003)).

One approach to skin lightening is to inhibit melanin synthesis by suppressing the activity, expression, and/or transcription of tyrosinase or other melanogenesis-related enzymes. However, current depigmenting agents have one or more shortcomings including toxicity, poor stability, low effectiveness, and side effects such as allergy and skin irritation. For example, hydroquinone and its derivatives are widely used in the treatment of hyperpigmentation, but the concentrations are strictly regulated due to their cytotoxicity and side effects such as permanent hypomelanosis and amelanosis (Smith C J, et al., *Pigment Cell Res*, 1(6):386-9 (1988)). In the United States, hydroquinone is available in concentrations up to 2% as an over-the-counter (OTC) drug, and the higher concentrations are only available by prescription (Engasser P, et al., *Journal of the American Academy of Dermatology*, 5(2):143-7 (1981)). Ascorbic acid and its derivatives can inhibit melanin synthesis, but they are unstable in air and high temperature and are unsuitable for regular storage. In particular, L-ascorbic acid quickly oxidizes and decomposes in aqueous solution, and is therefore not generally used as a depigmentating agent (Kameyama K, et al, *J. Am. Aca. Dermatol.*, 17:381-386 (1996)). Kojic acid and arbutin are used in skin lightening product (Majmudar G, et al, *J. Cosmet. Sci.*, 49:361-367 (1998); Maeda K, et al., *J. Pharmacol Exp Ther*, 276(2):765-9 (1996)), but a high concentration is required for them to exhibit inhibitory activities. Besides, kojic acid may also induce allergy. Azelaic acid and α-hydroxy acids may contribute to even skin tone, but often cause skin irritation. Other plant extracts or polyphenols have also been tested based on mushroom tyrosinase system, but their assays in cell-based systems are rare (Solano F., et al., *Pigment Cell Res*, 19(6):550-71 (2006)).

Agents to diminish melanin levels through other mechanisms may have high toxicity. A melanosome is an organelle found in animal cells and is the site for synthesis, storage and transport of melanin. Verapamil and rapamycin are two autophagy inducers, shown to possess autophagic effect by promoting the autophagic degradation of melanosomes in keratinocytes (Murase D, et al, *Journal of Investigative Dermatology*, 133:2416-24 (2013)). Similarly, resveratrol, was shown to increase autophagy in melanocytes, but the required concentration was very high (Kim E S, et al., *Experimental Dermatology*, 23:204-6).

Therefore, it is an object of the present invention to provide a composition and a method to safely and effectively lighten skin tone, reduce hyperpigmentation, or both.

It is another object of the present invention to provide a method of skin lightening, depigmentation, or both, through inhibiting the synthesis of melanin and inducing the autophagy of melanosome.

It is yet another object of the present invention to provide a composition and a method to suppress melanogenesis and accelerate the reduction of synthesized melanin.

SUMMARY OF THE INVENTION

A composition and its use to lighten skin, reduce hyperpigmentation, or both on the mammalian body surface are provided. The composition includes one or more compounds having the structure of Formula 1

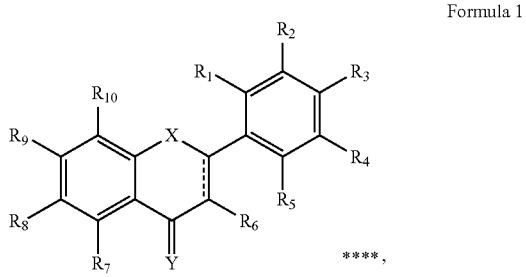

Formula 1 where $R_1$-$R_{10}$ are independently hydrogen, halogen, or substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl, where at least one of $R_8$ and $R_{10}$ is alkenyl substituted with heteroalkyl, cycloalkyl, heterocycloalkyl, cycloalkenyl, heterocycloalkenyl, aryl, heteroaryl, alkylaryl, alkylheteroaryl, arylalkyl, or heteroarylalkyl; X is O, S, NH, $CR_{11}R_{12}$, or $NR_{13}$, where $R_{11}$-$R_{13}$ are independently hydrogen or substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl; and Y is O, S, or N. In one embodiment, the one or more compounds having the structure of Formula 1 are used in an effective amount.

The composition can also include a compound according to Formula 1 in its stereoisomeric or tautomeric forms, in any of its stereoisomeric and tautomeric forms in any combination and in any ratio, a pharmaceutically acceptable salt thereof, a pharmaceutically acceptable solvate thereof, a pharmaceutically acceptable polymorph thereof, or a prodrug thereof.

In some forms, X and Y are O; the alkenyl of at least one of $R_8$ and $R_{10}$ is substituted with aryl or heteroaryl, preferably $C_2$-$C_{10}$ alkenyl, more preferably at $R_8$. In preferred forms, the compound has the structure of Formula 2 or Formula 3,

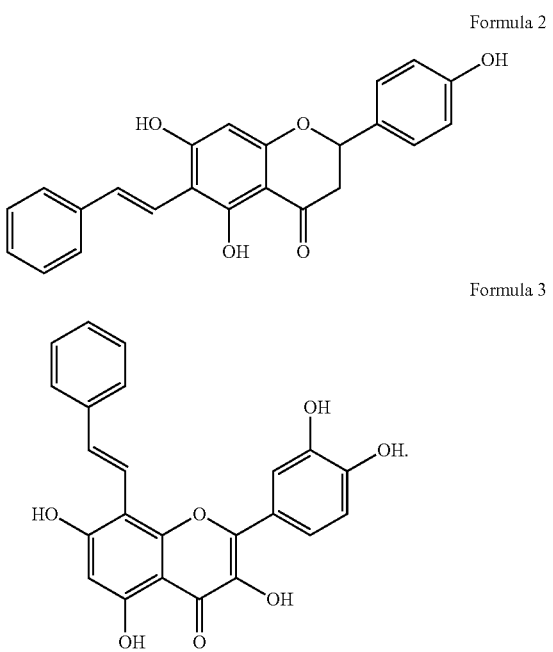

Formula 2

Formula 3

In some forms, the compound according to Formula 1 can be a derivative of polyphenol or a polyphenol having at least three hydroxyl groups, preferably at positions selected from $R_1$-$R_7$ and $R_9$. In some forms, the compound according to Formula 1 can have a double bond between carbon 2 and carbon 3 of the fused ring. In some forms, the compound according to Formula 1 can have a single bond between carbon 2 and carbon 3 of the fused ring. In some forms, the compound according to Formula 1 can have a double bond as the ═══ bond. In some forms, the compound according to Formula 1 can have a single bond as the ═══ bond.

The composition can be administered to a human or an animal via, for example, topical administration, injection to the dermal tissue, implantation under the skin, or oral administration, to reduce the synthesis of melanin and induce the autophagy of melanosome without causing cytotoxicity, thereby reducing the amount and distribution of melanin in the subject and lightening skin color or treating disorders associated with hyperpigmentation.

Generally, the composition can inhibit or reduce an activity, the expression, or an activity and the expression of tyrosinase, tyrosinase-related protein 1 (TRP-1), tyrosinase-related protein 2 (TRP-2), or a combination thereof, thereby preventing the darkening of body surface. The composition can also induces autophagy of melanosomes in the subject, thereby reducing the existing melanin and lightening hyperpigmented body surface area.

In some forms, the compound can be comprised in or derived from tomato extract, citrus extract, Herba Dendrobii extract, phenylalanine, or a mixture thereof. In some forms, the composition may further contain tomato extract, citrus extract, Herba Dendrobii extract, phenylalanine, or a mixture thereof. In some forms, the compound can be comprised in or derived from tomato extract, citrus extract, Herba Dendrobii extract, or a mixture thereof, in combination with phenylalanine. In some forms, the composition may further contain tomato extract, citrus extract, Herba Dendrobii extract, or a mixture thereof, in combination with phenylalanine.

In some forms, the composition can be generally free of cytotoxicity and effective in mitigating, preventing, treating, or a combination thereof, one or more skin conditions such as solar lentigines, melasma, freckles, discoloration, post-inflammatory hyperpigmentation, and combinations thereof.

In one embodiment, the present invention provides a method of lightening skin, reducing hyperpigmentation, or both in an area of a skin of a subject, comprising administering to the subject a composition according to the present invention. Preferably, wherein the administration of the composition reduces the synthesis of melanin in the subject, reduces the amount of melanin in the subject, limits the distribution of melanin in the subject, or a combination thereof; or wherein the administration of the composition inhibits or reduces an activity, the expression, or an activity and the expression of tyrosinase, tyrosinase-related protein 1, tyrosinase-related protein 2, or a combination thereof; or wherein the administration of the composition induces autophagy of melanosomes in the subject; or wherein the administration of the composition does not cause cytotoxicity in the subject; or wherein the composition is administered by topical application to body surface, injection to the dermal tissue, implantation under skin, of a combination thereof; or wherein the composition further comprises tomato extract, citrus extract, Herba Dendrobii extract, phenylalanine, or a mixture thereof; or wherein the administration of the composition is effective in mitigating, preventing, treating, or a combination thereof, one or more skin conditions selected from the group consisting of solar lentigines, melasma, freckles, discoloration, post-inflammatory hyperpigmentation, and combinations thereof.

In one embodiment, the present invention provides the use of the compound or the composition according to the present invention in the manufacture of a medicament or phrameuctical composition (1) to safely and effectively lighten skin tone, reduce hyperpigmentation, or both, (2) to suppress melanogenesis and accelerate the reduction of synthesized melanin, (3) for skin lightening, depigmentation, or both, through inhibiting the synthesis of melanin and inducing the autophagy of melanosome, or (4) for use in the method according to the present invention.

BRIEF DESCRIPTION OF THE DRAWINGS

FIG. 1A shows the results after a 72-hour treatment of melan-a cells with 6-C-(E-phenylethenyl)-naringenin (6-CEPN) at 0.0, 10.0, and 20.0 µM in the presence of α-melanocyte-stimulating hormone (α-MSH). FIG. 1B shows the results after a 72-hour treatment of melan-a cells with 8-C-(E-phenylethenyl)-quercetin (8-CEPQ) at 0.0, 2.5, and 5.0 µM in the presence of α-MSH. FIG. 1C shows the results after a 72-hour treatment of melan-a cells with kojic acid at 0.0, 10.0, and 20.0 µM in the presence of α-MSH. Each value is presented as mean±S.D. from triplicate independent experiments. Control cells were cells treated with α-MSH only for 72 hours.

FIG. 3A is a dot graph showing the change in L* (denoted as ΔL) of Melano-Derm™ (MEL-300-A, containing normal human derived melanocytes derived from Asian) skin model treated with vehicle (no test agent), rapamycin (2.5 µM) with vehicle, 6-CEPN (10 µM) with vehicle, or 8-CEPQ (5 µM) with vehicle. The lighter the skin color, the greater the L* value, hence a positive ΔL. FIG. 3B is a bar graph showing the tissue viability (%) of MelanoDerm™ treated with vehicle (no test agent), rapamycin (2.5 µM), 6-CEPN (10 µM), or 8-CEPQ (5 µM). The amount of viable tissue of vehicle-treated MelanoDerm™ is considered 100%. FIG. 3C is a dot graph showing the total melanin content (%) of Melano-Derm™ treated with vehicle (no test agent), rapamycin (2.5 µM), 6-CEPN (10 µM), or 8-CEPQ (5 µM). The amount of total melanin content of vehicle-treated MelanoDerm™ is considered 100%.

DETAILED DESCRIPTION OF THE INVENTION

Figure 1A:
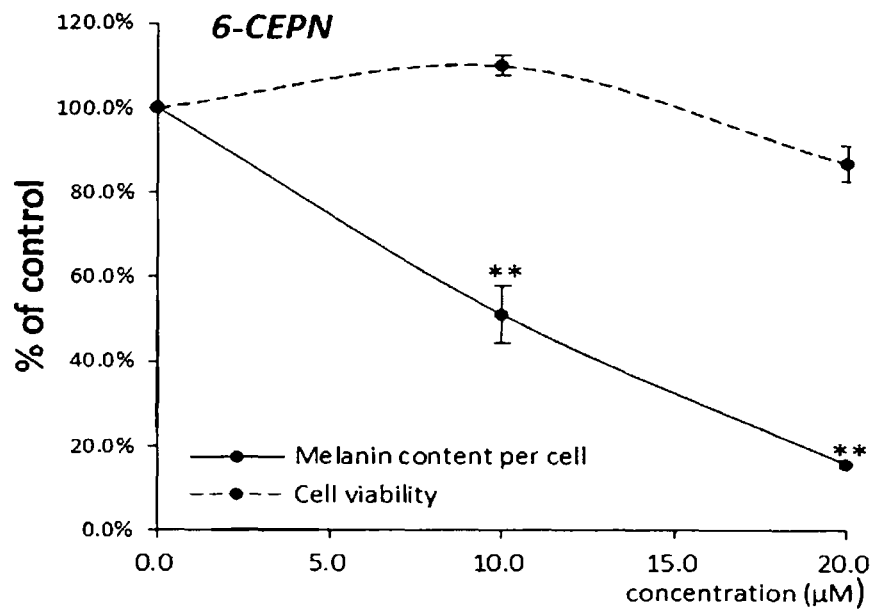
FIGS. 1A, 1B and 1C are line graphs showing cell viability or melanin content per cell as a percentage of control cells over different concentrations of test agents.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

I. Definitions

"Effective amount," as used herein, refers to an amount sufficient to induce one or more biological effects. Non-limiting examples of biological effects include a change in skin color, a change in the synthesis of melanin (either in vitro or in vivo) such as a decrease in melanin synthesis, a change in the viability of melanosome.

"Extract," as used herein in reference to a material derived from a plant material, refers to material that may be obtained by the following procedure: Place the indicated portion of dried plant material (stem, bark, leaves, etc.) in a conical glass percolator. Add the indicated percentage of extraction solvent in a w/w ratio such as 1 part plant material to 2 parts extraction solvent. When the indicated percentage of extraction solvent is less than 100%, the remaining solvent is water (e.g., 95% ethanol with 5% water, 50% ethanol with 50% water, etc.). Allow the extraction to proceed for about 16 to about 24 hours. Collect the percolate, and repeat the above process until the resulting percolate is substantially free from plant additional extract. Combine the percolates, evaporate to dryness under reduced pressure, and store the resulting extract under nitrogen at less than 4° C.

"Hyperpigmentation," as used herein, refers to an area of skin where the pigmentation is greater than that of an adjacent area of skin (e.g., a pigment spot, an age spot, and the like).

"Improve skin condition" or "improving skin condition," as used herein, refers to effecting a visually perceptible positive change, or benefit, in skin appearance. Benefits that may be provided include, but are not limited to, skin lightening and reducing discoloration caused by hyperpigmentation.

"Salts," as used herein, include, but are not limited to, sodium, potassium, calcium, ammonium, manganese, copper, and/or magnesium salts of a given chemical.

"Skin care actives" means chemicals that, when applied to the skin, provide a benefit or improvement to the skin. It is to be understood that skin care actives are useful not only for application to skin, but also to hair, nails and other keratinous tissue.

"Substituted," as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Aryl," as used herein, refers to $C_5$-$C_{26}$-membered aromatic, fused aromatic, fused heterocyclic, or biaromatic ring systems. Broadly defined, "aryl," as used herein, includes 5-, 6-, 7-, 8-, 9-, 10-, 14-, 18-, and 24-membered single-ring aromatic groups, for example, groups of benzene, naphthalene, anthracene, phenanthrene, chrysene, pyrene, corannulene, coronene, etc.

"Aryl" further encompasses polycyclic ring systems having two or more cyclic rings in which two or more carbons are common to two adjoining rings (i.e., "fused rings") where at least one of the rings is aromatic, e.g., the other cyclic ring or rings can be cycloalkyls, cycloalkenyls, cycloalkynyls, aryls and/or heterocycles.

The term "substituted aryl" refers to an aryl group, where one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle," "heterocyclic," and "heterocyclyl" are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) where Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with an heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics." "Heteroaryl" further encompasses polycyclic ring systems having two or more rings in which two or more carbons are common to two adjoining rings (i.e., "fused rings") where at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl."

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Alkyl," as used herein, refers to the radical of saturated aliphatic groups, including straight-chain alkyl, alkenyl, or alkynyl groups, branched-chain alkyl, cycloalkyl (alicyclic), alkyl substituted cycloalkylgroups, and cycloalkyl substituted alkyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfoxide, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', where R and R' are independently hydrogen, alkyl, or aryl, and where the nitrogen atom is optionally quaternized; —SR, where R is hydrogen, alkyl, or aryl; —CN; —NO$_2$; —COOH; carboxylate; —COR, —COOR, or —CON(R)$_2$, where R is hydrogen, alkyl, aryl, azide, aralkyl, alkoxyl, imino, phosphonate, phosphinate, silyl, ether, sulfonyl, sulfonamido, heterocyclyl, aromatic or heteroaromatic moieties, haloalkyl (such as —CF$_3$, —CH$_2$—CF$_3$, —CCl$_3$), —CN, —NCOCOCH$_2$CH$_2$, —NCOCOCHCH, —NCS, and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl, sulfoxide, and sulfonate), and silyl groups, as well as ethers, alkylthios, carbonyls (including ketones, aldehydes, carboxylates, and esters), haloalkyls, —CN and the like. Cycloalkyls can be substituted in the same manner.

The terms "alkenyl" and "alkynyl" refer to unsaturated aliphatic groups analogous in length and possible substitution to the alkyls described above, but that contain at least one double or triple bond, respectively.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quaternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quaternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenyl" is art recognized and refers to the aromatic moiety —C$_6$H$_5$, i.e., a benzene ring without one hydrogen atom.

The term "substituted phenyl" refers to a phenyl group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quaternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Amino" and "Amine," as used herein, are art-recognized and refer to both substituted and unsubstituted amines, e.g., a moiety that can be represented by the general formula:

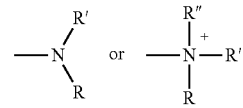

where, R, R', and R" each independently represent a hydrogen, substituted or unsubstituted alkyl, substituted or unsubstituted alkenyl, substituted or unsubstituted alkynyl, substituted or unsubstituted carbonyl, or —(CH$_2$)$_m$—R''', or R and R' taken together with the N atom to which they are attached complete a heterocycle having from 3 to 14 atoms in the ring structure; where R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R") each independently represent a hydrogen atom, substituted or unsubstituted alkyl, substituted or unsubstituted alkenyl, or —(CH$_2$)$_m$—R'''. Thus, the term 'alkylamine' as used herein refers to an amine group, as defined above, having a substituted or unsubstituted alkyl attached thereto (i.e., at least one of R, R', or R" is an alkyl group).

"Carbonyl," as used herein, is art-recognized and includes such moieties as can be represented by the general formula:

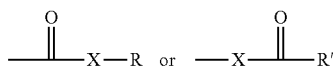

where X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, substituted or unsubstituted heteroaryl, —(CH$_2$)$_m$—R", or a pharmaceutical acceptable salt thereof; where R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, substituted or unsubstituted heteroaryl, or —(CH$_2$)$_m$—R"; where R" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate.' Where X is oxygen and R or R' is not hydrogen, the formula represents an "ester." In general, where the oxygen atom of the above formula is replaced by a sulfur atom, the formula represents a 'thiocarbonyl' group. Where X is sulfur and R or R' is not hydrogen, the formula represents a 'thioester.' Where X is sulfur and R is hydrogen, the formula represents a 'thiocarboxylic acid.' Where X is sulfur and R' is hydrogen, the formula represents a 'thioformate.' Where X is a bond and R is not hydrogen, the above formula represents a 'ketone.' Where X is a bond and R is hydrogen, the above formula represents an 'aldehyde.'

The term "substituted carbonyl" refers to a carbonyl, as defined above, where one or more hydrogen atoms in R, R' or a group to which the moiety

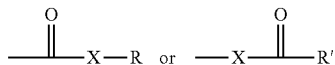

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "carboxyl" is as defined above for the formula

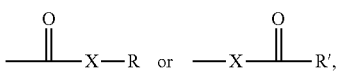

and is defined more specifically by the formula —R$^{iv}$COOH, where R$^{iv}$ is an alkyl, alkenyl, alkynyl, cycloalkyl, heterocyclyl, alkylaryl, arylalkyl, aryl, or heteroaryl. In preferred embodiments, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls and heteroaryls have from 3-10 carbon atoms in their ring structure, and more preferably have 5, 6 or 7 carbons in the ring structure.

The term "substituted carboxyl" refers to a carboxyl, as defined above, where one or more hydrogen atoms in R$^{iv}$ are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Heteroalkyl," as used herein, refers to straight or branched chain, or cyclic carbon-containing radicals, or combinations thereof, containing at least one heteroatom. Suitable heteroatoms include, but are not limited to, O, N, Si, P and S, where the nitrogen, phosphorous and sulfur atoms are optionally oxidized, and the nitrogen heteroatom is optionally quaternized.

Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

The terms "alkoxyl" or "alkoxy" and "aroxy" or "aryloxy" generally describe compounds represented by the formula —OR$^v$, where R$^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits.

The term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenoxy" is art recognized, and refers to a compound of the formula —OR$^v$ where R$^v$ is phenyl (i.e., —O—C$_6$H$_5$). One of skill in the art recognizes that a phenoxy is a species of the aroxy genus.

The term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The terms "aroxy" and "aryloxy," as used interchangeably herein, are represented by —O-aryl or —O-heteroaryl, where aryl and heteroaryl are as defined herein.

The terms "substituted aroxy" and "substituted aryloxy," as used interchangeably herein, represent —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "alkylthio" refers to an alkyl group, as defined above, having a sulfur radical attached thereto. The "alkylthio" moiety is represented by —S-alkyl. Representative alkylthio groups include methylthio, ethylthio, and the like. The term "alkylthio" also encompasses cycloalkyl groups having a sulfur radical attached thereto.

The term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phenylthio" is art recognized, and refers to —S—C$_6$H$_5$, i.e., a phenyl group attached to a sulfur atom.

The term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Arylthio" refers to —S-aryl or —S-heteroaryl groups, where aryl and heteroaryl as as defined herein.

The term "substituted arylthio" represents —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

"Arylalkyl," as used herein, refers to an alkyl group that is substituted with a substituted or unsubstituted aryl or heteroaryl group.

"Alkylaryl," as used herein, refers to an aryl group (e.g., an aromatic or hetero aromatic group), substituted with a substituted or unsubstituted alkyl group.

"Phenylalkyl," as used herein, refers to an alkyl group that is substituted with a substituted or unsubstituted phenyl or heterophenyl group.

"Alkylphenyl," as used herein, refers to an phenyl group, substituted with a substituted or unsubstituted alkyl group.

The terms "amide" or "amido," which are used interchangeably, refer to both "unsubstituted amido" and "substituted amido" and are represented by the general formula:

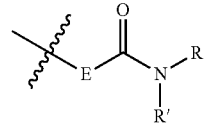

where E is absent or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, where independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, substituted or unsubstituted heteroaryl, or —(CH$_2$)$_m$R''', or R and R' taken together with the N atom to which they are attached complete a heterocycle having from 3 to 14 atoms in the ring structure; where R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' each independently represent a hydrogen atom, substituted or unsubstituted alkyl, a substituted or unsubstituted alkenyl, or —$(CH_2)_m$—R'''. When E is oxygen, a carbamate is formed. The carbamate cannot be attached to another chemical species, such as to form an oxygen-oxygen bond, or other unstable bonds, as understood by one of ordinary skill in the art.

The term "sulfonyl" is represented by the formula

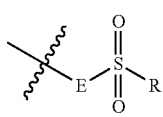

where E is absent or E is alkyl, alkenyl, alkynyl, aralkyl, alkylaryl, cycloalkyl, aryl, heteroaryl, heterocyclyl, where independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, substituted or unsubstituted heteroaryl, or —$(CH_2)_m$—R''', or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of E and R can be substituted or unsubstituted amine, to form a "sulfonamide" or "sulfonamido." The substituted or unsubstituted amine is as defined above.

The term "substituted sulfonyl" represents a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quaternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "sulfonic acid" refers to a sulfonyl, as defined above, where R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

The term "sulfate" refers to a sulfonyl, as defined above, where E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

The term "sulfonate" refers to a sulfonyl, as defined above, where E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, substituted or unsubstituted heteroaryl, or —$(CH_2)_m$—R'''; where R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

The term "sulfamoyl" refers to a sulfonamide or sulfonamide represented by the formula

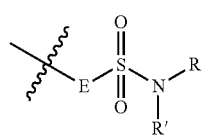

where E is absent or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, where independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, substituted or unsubstituted heteroaryl, or —$(CH_2)_m$—R''', or R and R' taken together with the N atom to which they are attached complete a heterocycle having from 3 to 14 atoms in the ring structure; where R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide.

The term "sulfoxide" is represented by the formula

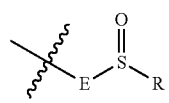

where E is absent or E is alkyl, alkenyl, alkynyl, aralkyl, alkylaryl, cycloalkyl, aryl, heteroaryl, heterocyclyl, where independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, substituted or unsubstituted heteroaryl, or —$(CH_2)_m$—R''', or E and R taken together with the S atom to which they are attached complete a heterocycle having from 3 to 14 atoms in the ring structure; where R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "phosphonyl" is represented by the formula

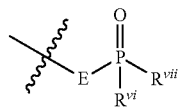

where E is absent or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, where, independently of E, $R^{vi}$ and $R^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, substituted or unsubstituted heteroaryl, or —(CH$_2$)$_m$—R''', or $R^{vi}$ and $R^{vii}$ taken together with the P atom to which they are attached complete a heterocycle having from 3 to 14 atoms in the ring structure; where R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

The term "substituted phosphonyl" represents a phosphonyl in which E, $R^{vi}$ and $R^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "phosphoryl" defines a phoshonyl in which E is absent, oxygen, alkoxy, aroxy, substituted alkoxy or substituted aroxy, as defined above, and independently of E, $R^{vi}$ and $R^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, $R^{vi}$ and $R^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof.

The term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

The term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

The terms "hydroxyl" and "hydroxy" are used interchangeably and are represented by —OH.

The terms "thiol" and "sulfhydryl" are used interchangeably and are represented by —SH.

The term "oxo" refers to =O bonded to a carbon atom.

The terms "cyano" and "nitrile" are used interchangeably to refer to —CN.

The term "nitro" refers to —NO$_2$.

The term "phosphate" refers to —O—PO$_3$.

The term "azide" or "azido" are used interchangeably to refer to —N$_3$.

The term "substituted $C_x$-$C_y$ alkyl" (where x and y are integers where x<y) refers to alkyl groups having from x to y carbon atoms, where at least one carbon atom is substituted. The term "unsubstituted $C_x$-$C_y$ alkyl" (where x and y are integers where x<y) refers to alkyl groups having from x to y carbon atoms that are not substituted.

The term "substituted $C_x$-$C_y$ alkylene" (where x and y are integers where x<y) refers to alkylene groups having from x to y carbon atoms, where at least one carbon atom is substituted. The term "unsubstituted $C_1$-$C_{10}$ alkylene" (where x and y are integers where x<y) refers to alkylene groups having from x to y carbon atoms that are not substituted. The term "alkylene" as used herein, refers to a moiety with the formula —(CH$_2$)$_a$—, where "a" is an integer from x to y.

The term "substituted $C_x$-$C_y$ alkenyl" (where x and y are integers where x<y) refers to alkenyl groups having from x to y carbon atoms, where at least one carbon atom is substituted. The term "unsubstituted $C_x$-$C_y$ alkenyl" (where x and y are integers where x<y) refers to alkenyl groups having from x to y carbon atoms that are not substituted.

The term "substituted $C_x$-$C_y$ alkynyl" (where x and y are integers where x<y) refers to alkynyl groups having from x to y carbon atoms, where at least one carbon atom is substituted. The term "unsubstituted $C_x$-$C_y$ alkynyl" (where x and y are integers where x<y) refers to alkynyl groups having from x to y carbon atoms that are not substituted.

The term "substituted $C_x$-$C_y$ alkoxy" (where x and y are integers where x<y) refers to alkoxy groups having from x to y carbon atoms, where at least one carbon atom is substituted. The term "unsubstituted $C_x$-$C_y$ alkoxy" (where x and y are integers where x<y) refers to alkoxy groups having from x to y carbon atoms that are not substituted. The terms "alkylamine" and "alkylamino" are used interchangeably. In any alkylamino, where the nitrogen atom is substituted with one, two, or three substitutents, the nitrogen atom can be referred to as a secondary, tertiary, or quarternary nitrogen atom, respectively.

The term "substituted $C_x$-$C_y$ alkylthio" (where x and y are integers where x<y) refers to alkylthio groups having from x to y carbon atoms, where at least one carbon atom is substituted. The term "unsubstituted $C_x$-$C_y$ alkylthio" (where x and y are integers where x<y) refers to alkylthio groups having from x to y carbon atoms that are not substituted.

The term "substituted $C_x$-$C_y$ carbonyl" (where x and y are integers where x<y) refers to carbonyl groups having from x to y carbon atoms, where at least one carbon atom is substituted. The term "unsubstituted $C_x$-$C_y$ carbonyl" (where x and y are integers where x<y) refers to carbonyl groups having from x to y carbon atoms that are not substituted.

The term "substituted $C_x$-$C_y$ carboxyl" (where x and y are integers where x<y) refers to carboxyl groups having from x to y carbon atoms, where at least one carbon atom is substituted. The term "unsubstituted $C_x$-$C_y$ carboxyl" (where x and y are integers where x<y) refers to carboxyl groups having from x to y carbon atoms that are not substituted.

The term "substituted $C_x$-$C_y$ amido" (where x and y are integers where x<y) refers to amido groups having from x to y carbon atoms, where at least one carbon atom is substituted. The term "unsubstituted $C_x$-$C_y$ amido" (where x and y are integers where x<y) refers to amido groups having from x to y carbon atoms that are not substituted.

The term "substituted $C_x$-$C_y$ sulfonyl" (where x and y are integers where x<y) refers to sulfonyl groups having from x to y carbon atoms, where at least one carbon atom is substituted. The term "unsubstituted $C_x$-$C_y$ sulfonyl" (where x and y are integers where x<y) refers to sulfonyl groups having from x to y carbon atoms that are not substituted.

The term "substituted $C_x$-$C_y$ sulfonic acid" (where x and y are integers where x<y) refers to sulfonic acid groups having from x to y carbon atoms, where at least one carbon atom is substituted. The term "unsubstituted $C_x$-$C_y$ sulfonic acid" (where x and y are integers where x<y) refers to sulfonic acid groups having from x to y carbon atoms that are not substituted.

The term "substituted $C_x$-$C_y$ sulfamoyl" (where x and y are integers where x<y) refers to sulfamoyl groups having from x to y carbon atoms, where at least one carbon atom is substituted. The term "unsubstituted $C_x$-$C_y$ sulfamoyl" (where x and y are integers where x<y) refers to sulfamoyl groups having from x to y carbon atoms that are not substituted.

The term "substituted $C_x$-$C_y$ sulfoxide" (where x and y are integers where x<y) refers to sulfoxide groups having from x to y carbon atoms, where at least one carbon atom is substituted. The term "unsubstituted $C_x$-$C_y$ sulfoxide" (where x and y are integers where x<y) refers to sulfoxide groups having from x to y carbon atoms that are not substituted.

The term "substituted $C_x$-$C_y$ phosphoryl" (where x and y are integers where x<y) refers to phosphoryl groups having from x to y carbon atoms, where at least one carbon atom is substituted. The term "unsubstituted $C_x$-$C_y$ phosphoryl" (where x and y are integers where x<y) refers to phosphoryl groups having from x to y carbon atoms that are not substituted.

The term "substituted $C_x$-$C_y$ phosphonyl" (where x and y are integers where x<y) refers to phosphonyl groups having from x to y carbon atoms, where at least one carbon atom is substituted. The term "unsubstituted $C_x$-$C_y$ phosphonyl" (where x and y are integers where x<y) refers to phosphonyl groups having from x to y carbon atoms that are not substituted.

The terms substituted "$C_x$ alkyl," "$C_x$ alkylene," "$C_x$ alkenyl," "$C_x$ alkynyl," "$C_x$ alkoxy," "$C_x$ alkylamino," "$C_x$ alkylthio," "$C_x$ carbonyl," "$C_x$ carboxyl," "$C_x$ amido," "$C_x$ sulfonyl," "$C_x$ sulfonic acid," "$C_x$ sulfamoyl," "$C_x$ phosphoryl," and "$C_x$ phosphonyl" (where x is an integer) refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms, where at least one carbon atom is substituted. The terms unsubstituted "$C_x$ alkyl," "$C_x$ alkylene," "$C_x$ alkenyl," "$C_x$ alkynyl," "$C_x$ alkoxy," "$C_x$ alkylamino", "$C_x$ alkylthio," "$C_x$ carbonyl," "$C_x$ carboxyl," "$C_x$ amido," "$C_x$ sulfonyl," "$C_x$ sulfonic acid," "$C_x$ sulfamoyl," "$C_x$ phosphoryl," and "$C_x$ phosphonyl" (where x is an integer) refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms where none of the carbons are substituted.

II. Compounds and Compositions

A. Active Compounds

Polycyclic organic compounds are in general provided in an effective amount to lighten skin tone, reduce hyperpigmentation, or both. For, example the effective amount of the active compound in the composition according to the present invention is from about 0.01 wt % to about 50 wt %, preferably from about 0.1 wt % to about 20 wt %, more preferably from about 2 wt % to about 10 wt %, most preferably from about 5 wt % to about 10 wt % of the composition. These compounds have the structure of Formula 1

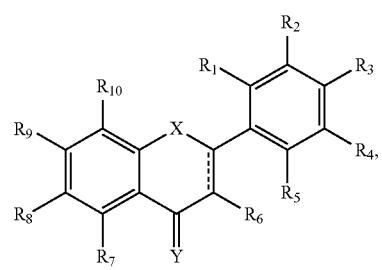

Formula 1 in any of its stereoisomeric and tautomeric forms in any combination and in any ratio, a pharmaceutically acceptable salt thereof, a pharmaceutically acceptable solvate thereof, a pharmaceutically acceptable polymorph thereof, or a prodrug thereof; where $R_1$-$R_{10}$ are independently hydrogen, halogen, or substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl; where at least one of $R_8$ and $R_{10}$ is alkyl or alkenyl substituted with alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl; X is O, S, NH, $CR_{11}R_{12}$, or $NR_{13}$, where $R_{11}$-$R_{13}$ are independently hydrogen or substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl; and Y is O, S, or N.

In some forms, at least one of $R_8$ and $R_{10}$ is alkyl or alkenyl substituted with heteroalkyl, cycloalkyl, heterocycloalkyl, cycloalkenyl, heterocycloalkenyl, aryl, heteroaryl, alkylaryl, alkylheteroaryl, arylalkyl, or heteroarylalkyl. In some forms, at least one of $R_8$ and $R_{10}$ is alkenyl substituted with heteroalkyl, cycloalkyl, heterocycloalkyl, cycloalkenyl, heterocycloalkenyl, aryl, heteroaryl, alkylaryl, alkylheteroaryl, arylalkyl, or heteroarylalkyl. In some forms, the at least one of $R_8$ and $R_{10}$ that is substituted alkenyl is a planar group (i.e., aromatic and double bonds constrain the atoms of $R_8$ and $R_{10}$ to lie in a single plane).

In some forms, X and Y of Formula 1 are O.

In some forms, the compounds having the structure of Formula 1 is a derivative of polyphenol or a polyphenol having at least three hydroxyl groups at positions selected from $R_1$-$R_7$ and $R_9$, most preferably at positions $R_3$, $R_7$, and $R_9$. In some forms, the compound according to Formula 1 can be a derivative of polyphenol or a polyphenol having at least four hydroxyl groups, preferably at positions selected from $R_1$-$R_7$ and $R_9$, most preferably at positions $R_3$, $R_6$, $R_7$, and $R_9$. In some forms, the compound according to Formula 1 can be a derivative of polyphenol or a polyphenol having at least five hydroxyl groups, preferably at positions selected from $R_1$-$R_7$ and $R_9$, most preferably at positions $R_2$, $R_3$, $R_6$, $R_7$, and $R_9$.

In some forms, the compound according to Formula 1 can have a double bond between carbon 2 and carbon 3 of the fused ring. In some forms, the compound according to Formula 1 can have a single bond between carbon 2 and carbon 3 of the fused ring. In some forms, the compound according to Formula 1 can have a double bond as the ⸺ bond. In some forms, the compound according to Formula 1 can have a single bond as the ⸺ bond.

In a preferred embodiment, the compounds having the structure of Formula 1 have a substituted alkenyl in at least one of $R_8$ and $R_{10}$ where the substituent is aryl or heteroaryl. In a further embodiment, the alkenyl of the at least one of $R_8$ and $R_{10}$ is $C_2$-$C_{10}$ alkenyl.

In some forms of the compound, the alkenyl of the at least one of $R_8$ and $R_{10}$ is substituted with aryl, heteroaryl, alkylaryl, alkylheteroaryl, arylalkyl, or heteroarylalkyl. In some forms, the alkenyl of the at least one of $R_8$ and $R_{10}$ is substituted with aryl or heteroaryl. In some forms, the alkenyl of the at least one of $R_8$ and $R_{10}$ is substituted with aryl. In some forms, the alkenyl of the at least one of $R_8$ and $R_{10}$ is substituted with phenyl. In some forms, the alkenyl of the at least one of $R_8$ and $R_{10}$ is $C_2$-$C_{10}$ alkenyl. In some forms, the alkenyl of the at least one of $R_8$ and $R_{10}$ is $C_2$-$C_5$ alkenyl. In some forms, the alkenyl of the at least one of $R_8$ and $R_{10}$ is $C_2$-$C_3$ alkenyl. In some forms, the alkenyl of the at least one of $R_8$ and $R_{10}$ is $C_2$ alkenyl.

In some forms of the compound, one of $R_8$ or $R_{10}$ is substituted alkenyl. In some forms, $R_8$ is substituted alkenyl. In some forms, $R_{10}$ is substituted alkenyl. In some forms, $R_8$ and $R_{10}$ are substituted alkenyl. In some forms, $R_{10}$ is hydrogen, $C_1$-$C_{10}$ alkyl, or $C_1$-$C_{10}$ alkyoxyl. In some forms, $R_8$ is hydrogen, $C_1$-$C_{10}$ alkyl, or $C_1$-$C_{10}$ alkyoxyl. In some forms, one of $R_8$ or $R_{10}$ is hydrogen, $C_1$-$C_{10}$ alkyl, or $C_1$-$C_{10}$ alkyoxyl. In some forms, one of $R_8$ or $R_{10}$ is hydrogen, $C_1$-$C_5$ alkyl, or $C_1$-$C_5$ alkyoxyl. In some forms, one of $R_8$ or $R_{10}$ is hydrogen, $C_1$-$C_3$ alkyl, or $C_1$-$C_3$ alkyoxyl. In some forms, one of $R_8$ or $R_{10}$ is hydrogen, $C_1$ alkyl, or $C_1$ alkyoxyl. In some forms, one of $R_8$ or $R_{10}$ is hydrogen.

In some forms of the compound, one of $R_8$ or $R_{10}$ is substituted alkyl. In some forms, $R_8$ is substituted alkyl. In some forms, $R_{10}$ is substituted alkyl. In some forms, $R_8$ and $R_{10}$ are substituted alkyl. In some forms of the compound, the alkyl of the at least one of $R_8$ and $R_{10}$ is substituted with aryl, heteroaryl, alkylaryl, alkylheteroaryl, arylalkyl, or heteroarylalkyl. In some forms, the alkyl of the at least one of $R_8$ and $R_{10}$ is substituted with aryl or heteroaryl. In some forms, the alkyl of the at least one of $R_8$ and $R_{10}$ is substituted with aryl. In some forms, the alkyl of the at least one of $R_8$ and $R_{10}$ is substituted with phenyl. In some forms, the alkyl of the at least one of $R_8$ and $R_{10}$ is $C_2$-$C_{10}$ alkyl. In some forms, the alkyl of the at least one of $R_8$ and $R_{10}$ is $C_2$-$C_5$ alkyl. In some forms, the alkyl of the at least one of $R_8$ and $R_{10}$ is $C_2$-$C_3$ alkyl. In some forms, the alkyl of the at least one of $R_8$ and $R_{10}$ is $C_2$ alkyl.

In some forms of the compound, at least one of $R_1$, $R_2$, $R_3$, $R_4$, $R_5$, $R_6$, $R_7$, and $R_9$ is —$NR_{14}R_{15}$, —$(CH_2)_m NR_{16}R_{17}$, —$NO_2$, —$CF_3$, —CN, —$C_2R_{18}$, —$SR_{19}$, —$N_3$ (e.g., azide), —$C(=O)NR_{20}R_{21}$, —$NR_{22}C(=O)R_{23}$, —$C(=O)R_{24}$, —$C(=O)OR_{25}$, —$OC(=O)R_{26}$, —$O(CR_{27}R_{28})_rC(=O)R_{29}$, —$O(CR_{30}R_{31})_rNR_{32}C(=O)R_{33}$, —$O(CR_{34}R_{35})_rNR_{36}SO_2R_{37}$, —$OC(=O)NR_{38}R_{39}$, —$NR_{40}C(=O)OR_{41}$, —$SO_2R_{42}$; —$SO_2NR_{43}R_{44}$, —$NR_{45}SO_2R_{46}$, or —$OR_{47}$; where m is 0, 1, or 2, where r is an integer from 1 to 6, and where $R_{14}$-$R_{47}$ are independently hydrogen or substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl.

In some forms of the compound, $R_1$, $R_2$, $R_3$, $R_4$, $R_5$, $R_6$, $R_7$, and $R_9$ are independently hydrogen, $C_1$-$C_{10}$ alkyl, or $C_1$-$C_{10}$ alkyoxyl. In some forms, six of $R_1$, $R_2$, $R_3$, $R_4$, $R_5$, $R_6$, $R_7$, and $R_9$ are independently $C_1$-$C_{10}$ alkyl or $C_1$-$C_{10}$ alkyoxyl and other is hydrogen. In some forms, five of $R_1$, $R_2$, $R_3$, $R_4$, $R_5$, $R_6$, $R_7$, and $R_9$ are independently $C_1$-$C_{10}$ alkyl or $C_1$-$C_{10}$ alkyoxyl and others are hydrogen. In some forms, four of $R_1$, $R_2$, $R_3$, $R_4$, $R_5$, $R_6$, $R_7$, and $R_9$ are independently $C_1$-$C_{10}$ alkyl or $C_1$-$C_{10}$ alkyoxyl and others are hydrogen. In some forms, three of $R_1$, $R_2$, $R_3$, $R_4$, $R_5$, $R_6$, $R_7$, and $R_9$ are independently $C_1$-$C_{10}$ alkyl or $C_1$-$C_{10}$ alkyoxyl and others are hydrogen. In some forms, two of $R_1$, $R_2$, $R_3$, $R_4$, $R_5$, $R_6$, $R_7$, and $R_9$ are independently $C_1$-$C_{10}$ alkyl or $C_1$-$C_{10}$ alkyoxyl and others are hydrogen. In some forms, one of $R_1$, $R_2$, $R_3$, $R_4$, $R_5$, $R_6$, $R_7$, and $R_9$ are independently $C_1$-$C_{10}$ alkyl or $C_1$-$C_{10}$ alkyoxyl and others are hydrogen. In some forms, $R_1$, $R_2$, $R_3$, $R_4$, $R_5$, $R_6$, $R_7$, and $R_9$ are hydrogen. In some forms, X, Y, $R_1$, $R_2$, $R_3$, $R_4$, $R_5$, $R_6$, $R_7$, and $R_9$ are not simultaneously O, O, H, H, H, H, H, H, and H, respectively.

In some forms of the compound, when X and Y in the compound of Formula 1 are O, at least two of $R_1$-$R_{10}$ are not hydrogen. In some forms of the compound, when X and Y in the compound of Formula 1 are O, at least one of $R_1$, $R_2$, $R_3$, $R_4$, $R_5$, $R_6$, $R_7$, and $R_9$ is not hydrogen. In some forms of the compound, when X and Y in the compound of Formula 1 are O, at least one of $R_1$, $R_2$, $R_3$, $R_4$, $R_5$, $R_6$, $R_7$, and $R_9$ is halogen, or substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl.

In some preferred forms, the compound is 6-C-(E-phenylethenyl)-naringenin (6-CEPN), having the structure of Formula 2, 8-C-(E-phenylethenyl)-naringenin (8-CEPN), or 8-C-(E-phenylethenyl)-quercetin (8-CEPQ), having the structure of Formula 3.

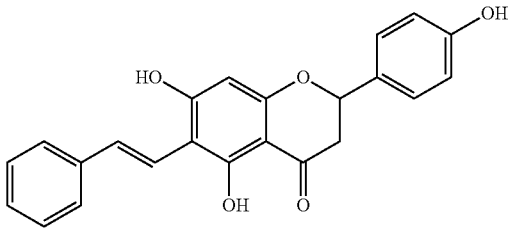 [SMILES: O=C1CC(c2ccc(O)cc2)Oc2cc(O)c(/C=C/c3ccccc3)c(O)c21]

Formula 2. Chemical structure of 6-C-(E-phenylethenyl)-naringenin (6-CEPN)

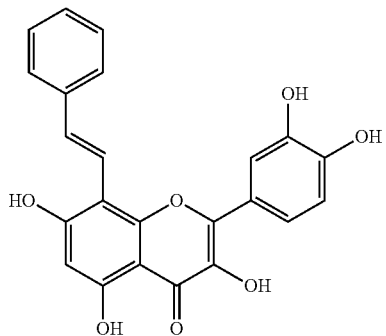 [SMILES: O=c1c(O)c(-c2ccc(O)c(O)c2)oc2c(/C=C/c3ccccc3)c(O)cc(O)c12]

Formula 3. Chemical structure of 8-C-(E-phenylethenyl)-quercetin (8-CEPQ).

Generally it is preferred that at least one of $R_8$ or $R_{10}$ is substituted alkenyl, where the substituent is hydrophobic, bulky, unsaturated, or a combination thereof.

Other examples include citrus, tomato, or Herba Dendrobii extracts, or derivatives thereof, more specifically flavonoids or derivatives of flavonoids such as naringenin (Chinese Patent Application Publication No. 104758191 A). Herba Dendrobii, known as Shi Hu in traditional Chinese medicine, is found in the stem of the orchid *Dendrobium nobile* Lindl and in many other orchid species of the *Dendrobium* genus. A preferred species as the source for Herba Dendrobii extract is *Dendrobium officinalis*. Other subgroups of flavonoids include flavones, flavonols, flavanols, flavanones, chalcones, aurones, isoflavones, anthocyanins, and proanthocyanidins. The derivation group preferably includes alkenyl and substituted alkenyl, where the substitution is cycloalkyl, heterocyclyl, cycloalkenyl, heterocycloalkenyl, aryl, heteroaryl, arylalkyl, heteroalkyls, alkylaryl, or alkylheteroaryl.

Naringenin reacts with phenylacetaldehyde via adduct formation, which forms 6-CEPN or 8-CEPN (Cheng K W, et al., *Chem. Res. Toxicol.*, 21(10):2026-2034 (2008)). Unlike some flavonones or their derivatives, which are capable of inhibiting cancer cells (Zang R, et al., *Process Biochemistry*, 48(1):78-88 (2013); Li H, et al., *Cancer Res*, 74(1):243-252 (2014)) or used as a tanning agent to promote the synthesis of melanoma cells (Bouzaiene N N, et al., *Life Sciences*, 144:80-85 (2016); Ohguchi K, et al., *Bioscience, Biotechnology, and Biochemistry*, 70(6):1499-1501 (2006)), the compound described here are able to lighten skin and reduce hyperpigmentation.

B. Formulations

The disclosed compositions containing the disclosed compound, such as compounds according to Formula 1 and isomers, analogs, or prodrugs of compounds according to Formula 1, or a pharmacologically active salt of the compound, can be formulated as pharmaceutical compositions, with, for example, one or more additional active agents, one or more pharmaceutically acceptable excipients, or both.

In some forms, the active compounds are formulated with controlled delivery vehicles for sustained delivery to a target area of the body surface.

a. Controlled Delivery Formulations

Controlled release polymeric devices can be used for long term release following administration of a polymeric device (rod, cylinder, film, disk) or injection (microparticles). The device can be in the form of microparticles (or nanoparticles) such as microspheres (nanosphere), where one of more compounds according to Formula 1 are dispersed within a solid polymeric matrix or capsules, where the core is of a different material than the polymeric shell, and the compound according to Formula 1 is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of compounds according to Formula 1, although biodegradable matrices are preferred. These may be natural or synthetic polymers, although synthetic polymers are preferred due to the better characterization of degradation and release profiles. The polymer can be selected based on the period over which release is desired. In some cases linear release may be useful, although in others a pulse release or "bulk release" may provide more effective results. The polymer may be in the form of a hydrogel (typically in absorbing up to about 90% by weight of water), and can optionally be complexed with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5,13-22 (1987); Mathiowitz, et al., *Reactive Polymers*, 6, 275-283 (1987); and Mathiowitz, et al., *J. Appl. Polymer Sci.*, 35, 755-774 (1988).

The devices can be formulated for local release to treat the body surface of interest, which will typically deliver a dosage that is much less than the dosage for treatment of an entire body or systemic delivery. These can be applied topically, injected into the dermal tissue, implanted or injected subcutaneously, into the muscle, fat, or swallowed.

b. Carriers or Excipients

Carriers or excipients for the one or more compounds according to Formula 1 are formed with materials that are generally recognized as safe. Carriers suitable for dermatological applications, injections, implantations, oral administration and other suitable routes administered to an individual without causing undesirable biological side effects or unwanted interactions.

Representative excipients include solvents, diluents, pH modifying agents, preservatives, antioxidants, suspending agents, wetting agents, viscosity modifiers, tonicity agents, stabilizing agents, and combinations thereof.

A dermatologically acceptable carrier is suitable for application to the skin, has good aesthetic properties, is compatible with the active agents and any other components, and will not cause any untoward safety or toxicity concerns.

A safe and effective amount of carrier is from about 50% to about 99.99%, preferably from about 99.9% to about 80%, more preferably from about 98% to about 90%, most preferably from about 95% to about 90% of the composition.

The carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g, from about 100 cps to about 200,000 cps. These emulsions can also be delivered in the form of sprays using either mechanical pump containers or pressurized aerosol containers using conventional propellants. These carriers can also be delivered in the form of a mousse. Other suitable topical carriers include anhydrous liquid solvents such as oils, alcohols, and silicones (e.g., mineral oil, ethanol isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like). Examples of topical carrier systems useful in the present invention are described in the following four references all of which are incorporated herein by reference in their entirety: "Sun Products Formulary" Cosmetics & Toiletries, vol. 105, pp. 122-139 (December 1990); "Sun Products Formulary," Cosmetics & Toiletries, vol. 102, pp. 117-136 (March 1987); U.S. Pat. No. 4,960,764 to Figueroa et al., issued Oct. 2, 1990; and U.S. Pat. No. 4,254,105 to Fukuda et al., issued Mar. 3, 1981.

The carriers of the present invention can comprise from about 50% to about 99% by weight of the compositions of the present invention, preferably from about 75% to about 99%, and most preferably from about 85% to about 95%.

Preferred cosmetically, pharmaceutically, or both acceptable topical carriers include hydro-alcoholic systems and oil-in-water emulsions. When the carrier is a hydro-alcoholic system, the carrier can comprise from about 0% to about 99% of ethanol, isopropanol, or mixtures thereof, and from about 1% to about 99% of water. More preferred is a carrier comprising from about 5% to about 60% of ethanol, isopropanol, or mixtures thereof, and from about 40% to about 95% of water. Especially preferred is a carrier comprising from about 20% to about 50% of ethanol, isopropanol, or mixtures thereof, and from about 50% to about 80% of water. When the carrier is an oil-in-water emulsion, the carrier can include any of the common excipient ingredients for preparing these emulsions. A more detailed discussion of suitable carriers is found in U.S. Pat. No. 5,605,894 to Blank et al., and, U.S. Pat. No. 5,681,852 to Bissett, both of which are herein incorporated by reference in their entirety.

In some forms, the compositions are formulated for oral administration. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the present proteins and derivatives. See, e.g., Remington's Pharmaceutical Sciences, 18th Ed. (1990), Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). See also Marshall, K. In: Modern Pharmaceutics Edited by G. S. Banker and C. T. Rhodes, Chapter 10, 1979.

Other forms provide liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

c. Other Components

The skin lightening and depigmentation compositions may optionally include additional active agents. Non-limiting examples of such skin actives include vitamin B3 compounds such as those described in PCT application WO 97/39733, published Oct. 30, 1997, to Oblong et al., herein incorporated by reference in its entirety; hydroxy acids such as salicylic acid; exfoliation or desquamatory agents such as zwitterionic surfactants; sunscreens such as 2-ethylhexyl-p-methoxycinnamate, 4,4'-t-butyl methoxydibenzoyl-methane, octocrylene, phenyl benzimidazole sulfonic acid; sunblocks such as zinc oxide and titanium dioxide; anti-inflammatory agents; anti-oxidants/radical scavengers such as tocopherol and esters thereof; metal chelators, especially iron chelators; retinoids such as retinol, retinyl palmitate, retinyl acetate, retinyl propionate, and retinal; N-acetyl-L-cysteine and derivatives thereof; hydroxy acids such as glycolic acid; keto acids such as pyruvic acid; benzofuran derivatives; depilatory agents (e.g., sulfhydryl compounds); other skin lightening agents (e.g., arbutin, kojic acid, hydroquinone, ascorbic acid and derivatives such as ascorbyl phosphate salts, placental extract, and the like); anti-cellulite agents (e.g., caffeine, theophylline); moisturizing agents; anti-microbial agents; anti-androgens; and skin protectants. Mixtures of any of the above mentioned skin actives may also be used. A more detailed description of these actives is found in U.S. Pat. No. 5,605,894 to Blank et al. (previously incorporated by reference). Preferred skin actives include hydroxy acids such as salicylic acid, sunscreen, antioxidants and mixtures thereof.

Other conventional skin care product additives may also be included in the compositions of the present invention. For example, urea, guanidine, glycerol, petrolatum, mineral oil, sugar esters and polyesters, polyolefins, methyl isostearate, ethyl isostearate, cetyl ricinoleate, isononyl isononanoate, isohexadecane, lanolin, lanolin esters, cholesterol, pyrrolidone carboxylic acid/salt (PCA), trimethyl glycine (betaine), tranexamic acid, amino acids (e.g., serine, alanine, threonine, histidine), their salts, panthenol and its derivatives, collagen, hyaluronic acid, elastin, hydrolysates, primrose oil, jojoba oil, epidermal growth factor, soybean saponins, mucopolysaccharides, and mixtures thereof may be used.

Other suitable additives or skin actives are discussed in further detail in PCT application WO 97/39733, published Oct. 30, 1997, to Oblong et al., previously incorporated by reference in its entirety.

III. Methods of Using

A. Reducing Melanin Bioavailability

Melanin in the epidermis determines the wide variation in skin color. Melanocytes, the cells in charge of melanin biosynthesis, contain melanosomes, a distinct class of lysosome-related organelles derived from the endosomal compartment. Melanosomes contain a distinct set of melanin-synthesizing enzymes and related structural proteins involved in melanogenesis, including tyrosinase, DOPAchrome tautomerase, and Pme117 (GP100) (Murase D, et al., *Journal of Investigative Dermatology,* 133: 2416-2424 (2013)).

An effective amount of the compounds according to Formula 1, Formula 2, or Formula 3 is administered to a human, an animal, or a microorganism to reduce the activity, transcription, or expression levels or the distribution of melanin. In some forms, the formulation is effective in reducing the melanin content without causing cytotoxicity to the subject. In some forms, the formulation is effective in inhibiting the synthesis/deposition of melanin by inhibiting tyrosinase, tyrosinase-related protein 1 (TRP-1), tyrosinase-related protein-2 (TRP-2), microphthalmia-associated transcription factor (MITF), DOPAchrome tautomerase, and Pmel17 (an important melanosomal structural protein, GP100), or other proteins or molecules involved in the synthesis of melanin, as measured by colorimetric assays such as SRB assay, western blotting analysis, ELISA, immunohistochemistry, or other assays. Examples of some relevant assays for assessing these and other activities and effects can be found in the examples. The results of such assays can be used to define the activity and/or effects of all or subsets of the compounds and compossitions described herein. Molecules involved in the synthesis of melanin in tranformed microorganisms can be seen PCT application WO 1992000373, published Jan. 9, 1992, to Biosource Genetics Corp., which is incorporated by reference in its entirety.

In other forms, the formulation is used in lightening the affected body surface area, reducing the size of the hyperpigmentation body surface area, and reducing the severeness of disorders or discomfort associated with the skin tone or hyperpigmentation of the subject.

B. Inducing Melanosome Autography

Melanocytes transfer melanosomes through their dendrites to keratinocytes, where they form the melanin caps that reduce UV-induced DNA damage in human epidermis (Costin G E, et al., *The FASEB Journal,* 21(4):976-994). The skin's layers are represented by the epidermis, the dermis, and the hypodermis, the latter consisting of fatty tissue that connects the dermis to underlying skeletal components.

An effective amount of the compounds according to Formula 1, Formula 2, or Formula 3 can be administered to a human or an animal to induce the autophagy of melanosome, thereby reducing the synthesis, storage, transport, or a combination thereof, of melanin.

C. Manners of Administration

The compositions are useful for topical application, dermal injection, implantation under skin, oral administration, and other relevant routes of administration for regulating mammalian skin condition (especially human skin, more especially human facial skin), including but not limited to skin lightening and reduction of hyperpigmentation. Regulating skin condition includes prophylactically treating, cosmetically altering, therapeutically regulating skin condition, or combinations thereof. As used herein, prophylactically regulating skin condition includes delaying, minimizing, preventing darkening in skin, or combinations thereof. As used herein, cosmetically altering skin condition includes lightening the skin tone. As used herein, therapeutically regulating skin condition includes ameliorating, e.g., diminishing or minimizing, skin pigment disorders. Regulating skin condition involves improving skin appearance, feel, or combinations thereof.

Regulating skin condition involves topically applying to the skin a safe and effective amount of a composition of the present invention. The amount of the composition which is applied, the frequency of application and the period of use will vary widely depending upon the level of the compound according to Formula 1 and/or other components of a given composition and the level of regulation desired, e.g., in light of the level of skin aging present in the subject and the rate of further skin aging.

In a preferred embodiment, the composition is chronically applied to the skin or applied until desirable results are obtained as decided by the user or medical practioner. "Chronic application" is meant continued application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), it is preferred that chronic application continue throughout the subjects lifetime. Typically applications would be on the order of about once per day over such extended periods, however application rates can vary from about once per week up to about three times per day or more.

D. Conditions or Disorders to be Treated

Examples of skin conditions that can be regulated by the disclosed composition include reducing post-inflammatory hyperpigmentation, regulating discoloration of skin, solar lentigines, melasma, and freckles.

Other associated benefits of the cosmetic formulations includes regulating moisturization and barrier properties of skin, regulating epidermal differentiation of skin, regulating exfoliation of skin, thickening of skin to reduce skin atrophy, regulating the elasticity of skin, reducing oily skin, regulating cellulite in skin, regulating pruritus in skin, and promoting wound healing in skin.

E. Dosage and Effective Amount

A wide range of quantities of the compositions of the present invention can be employed to provide a skin appearance benefit. Quantities of the present compositions which are typically applied per application are, in mg composition/$cm^2$ skin, from about 0.1 $mg/cm^2$ to about 10 $mg/cm^2$. A particularly useful application amount is about 2 $mg/cm^2$. Alternatively, the active agents in the final composition may be between about 1 µM and about 10 mM, preferably between about 1 µM and about 1 mM, and most preferably between about 10 µM and about 200 µM.

Regulating skin condition is preferably practiced by applying a composition in the form of a skin lotion, cream, gel, emulsion, spray, conditioner, cosmetic, lipstick, foundation, nail polish, or the like which is intended to be left on the skin for some esthetic, prophylactic, therapeutic or other benefit (i.e., a "leave-on" composition). After applying the composition to the skin, it is preferably left on the skin for a period of at least about 15 minutes, more preferably at least about 30 minutes, even more preferably at least about 1 hour, most preferably for at least several hours, e.g., up to about 12 hours. Any part of the external portion of the face, hair, and/or nails can be treated, e.g., face, lips, under-eye area, eyelids, scalp, neck, torso, arms, hands, legs, fingernails, toenails, scalp hair, eyelashes, eyebrows, etc.

Another approach to ensure a continuous exposure of the skin to at least a minimum level of the skin-lightening compound is to apply the compound by use of a patch applied, e.g., to the face. Such an approach is particularly useful for problem skin areas needing more intensive treatment. The patch can be occlusive, semi-occlusive or non-occlusive. The flavonoid compound composition can be contained within the patch or be applied to the skin prior to application of the patch. The patch can also include additional actives such as chemical initiators for exothermic reactions such as those described in PCT application WO 9701313 to Burkett et al. The patch is preferably left on the skin for a period of at least about 15 minutes, more preferably at least about 30 minutes, even more preferably at least about 1 hour, most preferably at night as a form of night therapy.

In some forms of treating skin disorders, the term "effective amount" or "therapeutically effective amount" means a dosage sufficient to treat, inhibit, or alleviate one or more symptoms of the disorder being treated or to otherwise provide a desired pharmacologic and/or physiologic effect. The amount of the one or more compounds according to Formula 1, Formula 2, or Formula 3 administered to a subject is typically enough to prevent, reduce, decrease, or inhibit the symptoms of hyperpigmentation-related disorders.

F. Controls

The effect of one or more compounds according to Formula 1, Formula 2, or Formula 3 can be compared to a control or to the subject's previous condition before treatment. For example, in some forms, one or more of the parameters affected by treatment with the compounds according to Formula 1, Formula 2, or Formula 3 is compared to the same parameters in untreated control subjects or in subjects before treatment. These parameters include but are not limited to the activity, transcription, or expression levels of melanin, the viability of melanosome, the measurement of affected body surface darkness, the size of the hyperpigmentation body surface area, and the severeness of disorders or discomfort associated with the skin tone or hyperpigmentation of the subject. In preferred embodiments the control subject suffers the same disorders, discomfort, or conditions as the treated subject.

Alternatively, subjects treated with one or more compounds according to Formula 1, Formula 2, or Formula 3, or an analog or prodrug thereof, can be compared to subjects treated with pharmaceutical agents known to prevent, reduce or decrease the symptoms of myocardial infarction or other macrophage-mediated inflammatory disorders.

The subjects treated can have one or more of the following benefits: reduction in the activity, transcription, or expression levels or distribution of melanin, reduction in the viability of melanosome or translocation of melanosome, lighter skin tone of the body surface, smaller size of the hyperpigmentation body surface area, and the reduction of the severeness of disorders or discomfort associated with the skin tone or hyperpigmentation.

EXAMPLES

Example 1

No Apparent Cytotoxicity Associated with 6-CEPN and its Significant Efficacy in Reducing Melanin Synthesis Materials and Methods Cell Culture and Treatment Murine melan-a cells (an immortalized, non-tumorigenic murine melanocyte cell line) were obtained from Chinese University of Hong Kong. Cells were cultured in RPMI 1640 medium. Culture medium was supplemented with 10% FBS and 1% penicillin-streptomycin and the cells were incubated at 37° C. in 5% $CO_2$. Melan-a cells were incubated with tetradecanoyl phorbol acetate (TPA) at a concentration of 200 nM. The tested chemical agents (e.g., 6-CEPN and Kojic acid) were individually dissolved as a stock solution at a concentration of 100 mM in 100% dimethyl sulfoxide (DMSO). The stock solution was diluted using culture medium to the desired final concentrations immediately prior to use. The final DMSO concentration did not exceed 0.1%.

Evaluation of Cell Survival Rate

Melan-a cells (10,000 cells/well) were plated in 100 μL 96-well multidishes for at least 24 hours (hrs) prior to use. The cells were treated with serial concentrations of tested chemicals for 72 hrs. After the indicated incubation time, cells were washed three times using PBS and then treated with CCK-8 solution (0.5 mg/mL) for 1.5 hours. Absorbance was measured at 490 nm using Victor X4 Multilabel Plate Reader (PerkinElmer, Mass., USA). Values were expressed as the mean cell viability as a percentage of that of the vehicle DMSO (0.1% final volume)-treated cultures.

Measurement of Cellular Melanin Content

Melan-a cells ($3\times10^5$ cells/well) were plated in 2 mL of 12-well multidishes for at least 24 hrs prior to use. The cells were treated with α-melanocyte-stimulating hormone (α-MSH) (1 μM) alone or with α-MSH (1 μM) plus different concentrations of chemical agents for 72 hrs. Melanin content was measured using a sulphorhodamine B (SRB) combined assay (Lam R Y et al., *J Ethnopharmacol*, 132(1): 274-9 (2010); Chinese patent application publication no. CN 104758191 A) to ensure any reduction in the melanin content was not due to the death of melan-a cells. As the colorimetric-based SRB assay could accurately estimate the number of viable cells, the melanin level was expressed as melanin content versus each single cell by taking into account the results of viable cells from the SRB assay. In brief, melan-a and b16 cells (3×105 cells/well) were plated in 2 mL of 12-well multidishes for at least 24 h prior to use. The cells were treated with α-MSH (1 μM) alone or with α-MSH plus serial concentrations of agents for 72 h. After a 72 h incubate, cell number was counted using SRB assay. 250 μL of cold (4° C.) TCA were added to each well to fix cells. One hour after the fixation, the plate was washed 5 times with PBS to remove TCA, medium, and dead cells. After drying the plate in the air, the cells were incubated with 500 μL/well of 0.4% w/v SRB in 1% acetic acid to stain the cells for 30 mins. Subsequently, the plate was washed with 1% acetic acid ten times to remove the unbound SRB dye thoroughly. 300 μL of 10 mM aqueous trisbase was then added to each well to solubilize the cell-bound dye. After 15 mins on a gyratory shaker, the solubilized dye was transferred to a 96-well plate. The OD value was read at 595 nM. As previously determined, there is a superb linearity between cell number and absorbance reading. Therefore, the OD value of SRB assay dye presents the number of cells in each well. The fixing step of the SRB method allows the amount of melanin in cells to be measured after the completion of SRB assay. The remaining cells were then collected by trypsinization and centrifuged at 13500 g for 10 mins. The major supernatant was removed and the remaining cell residues were dried in a freeze-dryer. After this, 150 µL of 1 N NaOH was added to each microtubule to lyse the cells for the release of melanin. Melanin solution was transferred to a 96-well plate and the absorbance value was measured at 490 nm using Victor X4 Multilabel Plate Reader (PerkinElmer, Mass., USA).

Results

As shown in FIG. 1A, there was no significant decrease on the cell survival rate after treatment with 6-CEPN at a concentration equal to or lower than 20 µM. This shows that 6-CEPN is safe to apply to cells at least when used at a concentration equal to or lower than 20 µM.

Figure 1B:
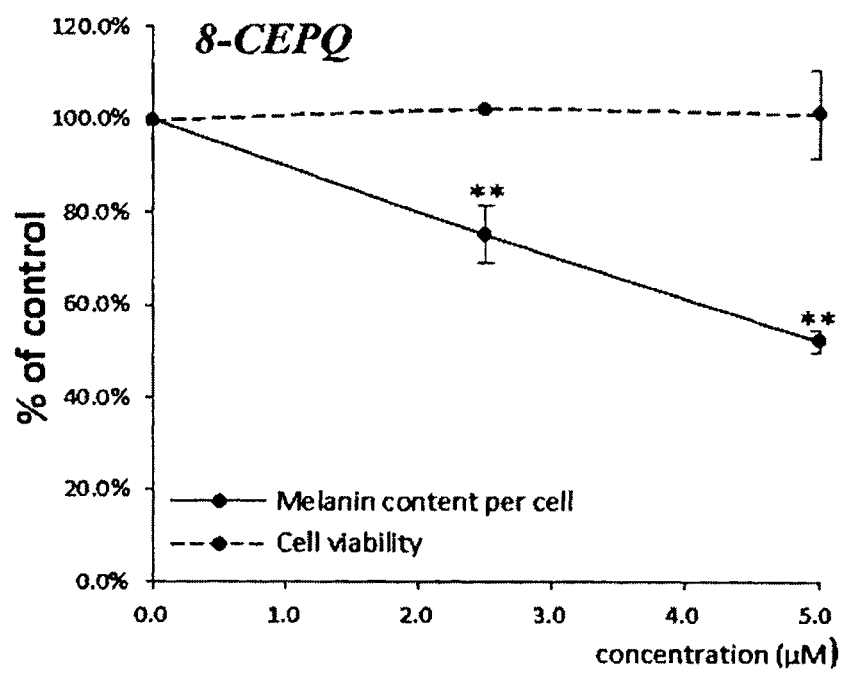
Figure 1C:
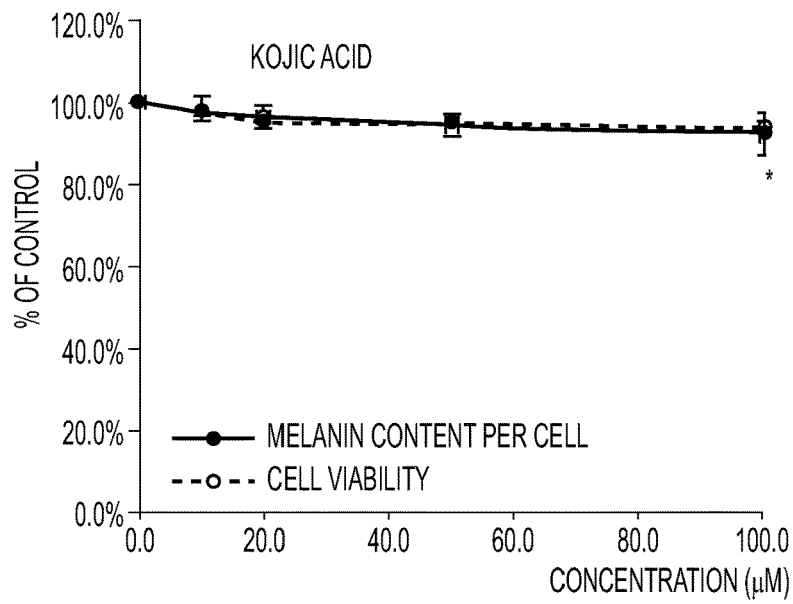

In melan-a cells, 6-CEPN showed much stronger depigmenting effects than kojic acid (FIGS. 1A and 1B). 6-CEPN induced nearly 80% depigmentation at the concentration of 20 µM. The inhibition was greater than many known melanogenesis inhibition agents such as kojic acid and arbutin in this cell line. 8-CEPQ presented similar results with 6-CEPN. Based on it, it was considered that 6-CEPN and 8-CEPQ not only inhibits melanogenesis, but also reduces already synthesized melanin.

Example 2

Inhibition of Tyrosinase and Tyrosinase-Related Proteins by 6-CEPN

Materials and Methods
Tyrosinase Activity Assay

Cellular tyrosinase activity was determined by measuring the oxidation of L-3,4-dihydroxyphenylalanine (L-DOPA) to dopachrome in cell lysates. Melan-a cells ($1.5 \times 10^5$ cells/well) were plated in 1 mL of culture medium in a 24-well multidishes for at least 24 hrs prior to use. The cells were treated with α-MSH (1 µM) alone or with α-MSH plus different concentrations of testing agents for 72 hrs. The cells were washed with cold PBS and lysed in 900 µL of PBS with 1% Triton X-100. After being freeze-thawed at −80° C. for 30 min followed by 25° C. for 30 min, 100 µL of 10 mM L-DOPA was then added to each well. Following incubation at 37° C. for 1 hr, the absorbance of the agents was measured at 490 nm using Victor X4 Multilabel Plate Reader (PerkinElmer, Mass., USA).

Western Blotting

Melan-a cells ($3 \times 10^5$ cells/well) were seeded in 4 mL of culture medium in a 6-well plate for at least 24 hrs prior to use. The cells were treated with α-MSH (1 µM) alone, α-MSH plus plus different concentration of agents for 72 hrs. The cells were washed with cold PBS and then lysed in 100 µL of RIPA buffer containing 1% Nonidet P-40, 0.1% sodium dodecylsulfate, 0.5% sodium deoxycholate, and 2% protease inhibitor at 4° C. Samples were centrifuged at 14,000 rpm for 30 mins at 4° C., and total proteins in the supernatant were separated. 10 µg of denatured proteins were loaded per lane, and separated by 10% SDS-PAGE gel. Proteins were then transferred to Immobilon-P Transfer Membranes (Millipore Co., Bed-ford, Mass.) by semidry transfer. Membranes were incubated with primary antibodies specific for Tyrosinase, tyrosinase-related protein-1 (TRP1), tyrosinase-related protein-2 (TRP2), and micropthalmia-associated transcription factor (MITF). The blots were subsequently washed and incubated with the appropriate secondary antibodies. Immunoreactive protein bands were visualized with enhanced chemiluminescence western blotting detection reagents and quantified using an ODYSSEY Fc Imaging system. The amounts of protein loaded were normalized against a control protein, β-actin.

Results

Figure 2A:
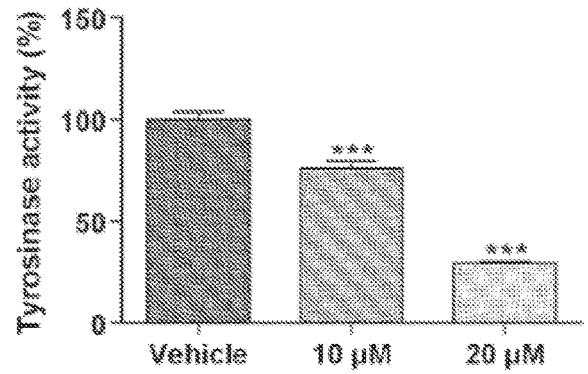
FIG. 2A is a bar graph showing the activity of tyrosinase (as a percentage, %, of that of control cells) in melan-a cells treated with differenct amounts of 6-CEPN.
Figure 2B:
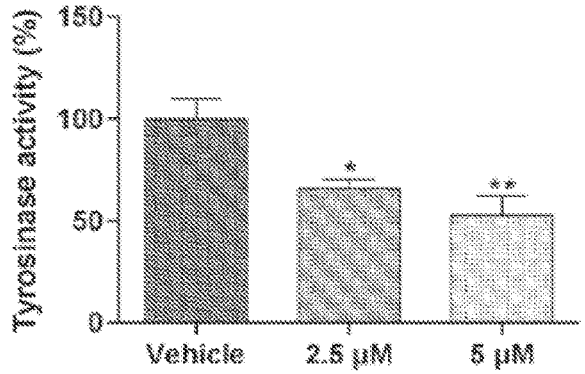
FIG. 2B is a bar graph showing the activity of tyrosinase (as a percentage, %, of that of control cells) in melan-a cells treated with differenct amounts of 8-CEPQ. Control cells were treated with α-MSH (vehicle) for 72 hrs, and tested cells were treated with α-MSH in combination with 10 µM or 20 µM 6-CEPN, or with 2.5 µM or 5 µM. Each value is presented as mean±S.D. from triplicate independent experiments. *Significant is denoted as $p<0.05$ vs control. ** Significant is denoted as $p<0.01$ vs control.

As shown in FIG. 2, 6-CEPN and 8-CEPQ presented significant inhibition on tyrosinase activity in a dose-dependent manner at micromolar levels. It is an excellent tyrosinase inhibitor.

Western blotting analysis at the concentration of 20 µM showed that the protein levels of tyrosinase, TRP-1, and TRP-2 were significantly suppressed by 6-CEPN. There was no clear inhibition on the expression of MITF.

Example 3

Induction of Autophagy of Melanosome by 6-CEPN and 8-CEPQ

Materials and Methods
Cell Treatment for Fluorescent Microscopy

Melan-a cells ($1.5 \times 10^5$ cells/well) were seeded on coverslips in 6-well palte. The cells were treated with (1) α-MSH (1 µM) alone for 24 hrs, (2) α-MSH (1 µM) plus rapamycin (0.5 µM) for 24 hrs, (3) α-MSH (1 µM) plus 6-CEPN (10 µM), or (3) α-MSH (1 µM) plus 8-CEPQ (5 µM) for 72 hrs. Culture medium was removed carefully after the cells reached 50%~70% level of confluence. Cells were stained by microscopy dual detection reagents (autophagy detection kit, Abcam) for 30 mins at 37° C. The stained cells were analyzed by wide-field fluorescence microscopy (60× magnification). Standard FITC filter and DAPI filter were set to image the autophagic signal and the nuclear signal, respectively.

siRNA Transfection and Western Blot Analysis

Melan-a cells ($3 \times 10^5$ cells/well) were seeded in a 6-well plate with 4 mL RPMI 1640 medium and 10% FBS. Melan-a cells were then transfected with 10 nM siRNA against autophagy-related protein 7 (ATG-7) or with the same concentration of a control siRNA, using HiPerfect Transfection Reagent. After 72 hrs of incubation, cell culture medium was replaced. Cells were then treated for 72 hrs with (1) α-MSH (1 µM) and TPA; (2) α-MSH (1 µM), TPA, and 6-CEPN (10 µM); or (3) α-MSH (1 µM), TPA, and 6-CEPN (20 µM). Total protein of cells was collected as described in the Western blotting in Example 2. The expressions of autophagy related proteins ATG-7 and microtubule-associated protein light chain 3 (LC-3) were analyzed by Western blot. LC-3 was selected because it was widely used to monitor autophagy. LC-3 can convert from a cytosolic form (i.e., LC-3 I) to a lipidated form (i.e., LC-3 II), the latter of which is attached to the autophagosome membrane (Mizushima N, et al., *Autophagy*, 3(6): 542-545 (2007)). ATG-7 is a required component in the conjugation of other autophagy-related proteins (e.g., the conjugation between ATG-12 and ATG-15), which ultimately leads to the formation of autophagosome ("Autophagy Signaling Pathway," Cell Signaling Technology, revised online October 2012).

Results

The induction of autophagy of melanosome by 6-CEPN and 8-CEPQ was detected using fluorescence microscopy. Rapamycin, a typical autophagy inducer which can diminish melanin levels in human skin substitutes, was used as positive control. Fluorescent microscopy analysis confirmed rapamycin, 6-CEPN and 8-CEPQ both induced melanosome autophagy in melan-a cells. These results indicate that induction of autophagy by 6-CEPN and 8-CEPQ contribute to the regulation of melanosome degradation, leading to the reduction of existing melanin.

These results show that 6-CEPN and 8-CEPQ have dual modes of action: to reduce the synthesis of melanin and to induce the autophagy of melanosome.

Western blotting analysis showed the reduced protein levels of ATG-7 and LC-3 II confirmed their autophagic effect. Suppression of autophagy-related protein 7 (ATG-7) expression by the specific siRNA remarkably decreased the amount of LC-3 II. Moreover, treatment with 6-CEPN increased the conversion of LC-3 I to LC-3 II.

This data, together with previous results using fluorescence microscopy, confirmed the autophagic effect of 6-CEPN.

Example 4

Depigmentation in an Artificial Skin Model

Materials and Methods

Epidermal equivalents containing melanocytes (Mel-300-A) were maintained according to the manufacturer's instructions. Mel-300-A tissue was cultured in EPI-100-NMM-113 medium for 14 days. Agents were dissolved in tissue culture medium and changed every other day. The test agents were either (1) rapamycin (2.5 µM), as the positive control in depigmentation, (2) 6-CEPN (10 µM), or (3) 8-CEPQ (5 µM). The concentration of rapamycin used was lower than 6-CEPN and 8-CEPQ, as rapamycin is toxic to cells at higher concentration. Pigmentation of these skin equivalents was compared against treatment of cells with a culture medium only (denoted as "vehicle"). Tissue viability was assessed on day 14 by CCK-8 assay as described in Example 1. On day 14, single tissues were harvested and photographed. The L* parameter was used to evaluate skin lightening or darkening. The lighter the skin, the greater the L* value. ΔL* value was measured by a Chroma Meter CR400 (Konica Minolta) for an evaluation of lightening as a function of time. Three tissues for each treatment were frozen for the Solvable Melanin assay (Bessou-Touya et al., "Chimeric human epidermal reconstructs to study the role of melanocytes and keratinocytes in pigmentation and photoprotection." Journal of investigative dermatology 111(6): 1103-1108 (1998)). Additional tissues were fixed by 10% formanin. For melanin staining in paraffin-embedded tissues, Fontana-Masson silver staining was used as previously detailed (Barbosa et al., "A simple and economical modification of the Masson-Fontana method for staining melanin granules and enterochromaffin cells." Stain technology 59(4):193-196 (1984)).

Results

Figure 3A:
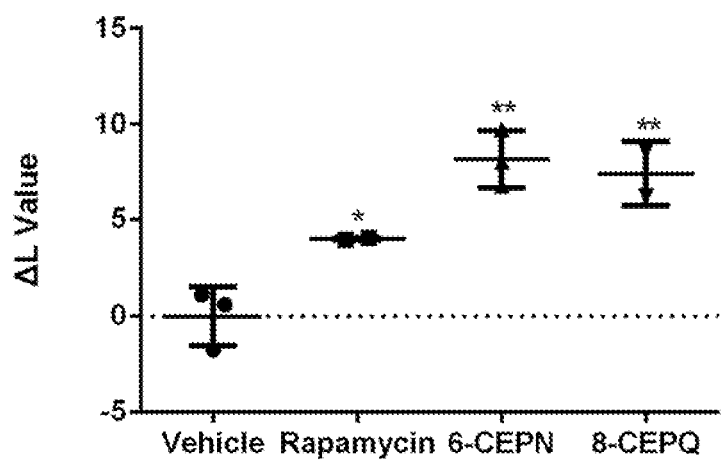
FIGS. 3A-3C are graphs features of 6-CEPN, 8-CEPQ and rapamycin in different assays.
Figure 3B:
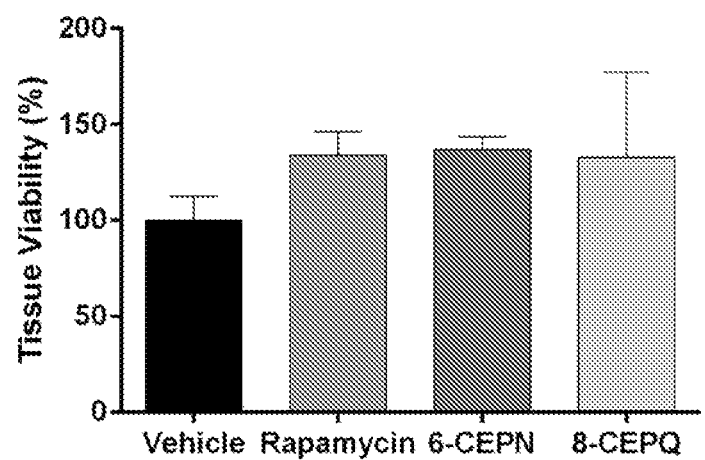
Figure 3C:
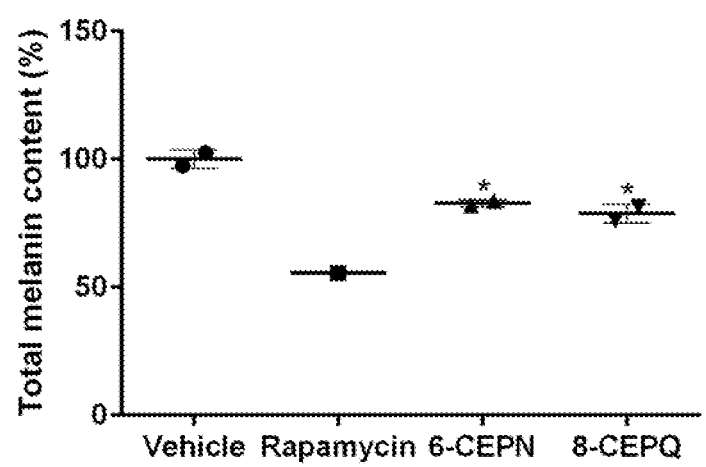

6-CEPN, 8-CEPQ and rapamycin both increased the brightness of the tissues, as confirmed by visual examination. As shown in FIGS. 3A and 3B, 6-CEPN, 8-CEPQ and rapamycin both increased the L* value when compared with negative control groups on day 14, without significant cytotoxicity during the whole treatment period. The results were similar on both day 10 and day 14. As shown in FIG. 3C, 6-CEPN, 8-CEPQ and rapamycin also significantly inhibited the amount of melanin in human skin equivalents. Fontana Masson staining on day 14 specimens confirmed an apparent, significant decrease in the melanin content and distribution in the 6-CEPN treated group without causing reduction in the thickness of basal layer of tissue. In comparison, no melanin was observed in rapamycin-treated group, but the thickness of basal layer of tissue was thinner than 6-CEPN-treated or non-treated control groups, indicating that rapamycin negatively influenced cell growth.

It is understood that the disclosed method and compositions are not limited to the particular methodology, protocols, and reagents described as these may vary. It is also to be understood that the terminology used herein is for the purpose of describing particular forms and embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, reference to "a compound" includes a plurality of molecules of such compound, reference to "the compound" is a reference to one or more compounds and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy

We claim:
1. A composition comprising
(a) a compound having the structure of Formula 1

Formula 1 stereoisomeric form thereof, tautomeric form thereof, a pharmaceutically acceptable salt thereof, a pharmaceutically acceptable solvate thereof, a pharmaceutically acceptable polymorph thereof, or a prodrug thereof; and
(b) a pharmaceutically acceptable excipient;
wherein
$R_1$-$R_{10}$ are independently hydrogen, halogen, hydroxyl, or substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl;
at least one of $R_8$ and $R_{10}$ is alkenyl substituted with heteroalkyl, cycloalkyl, heterocycloalkyl, cycloalkenyl, heterocycloalkenyl, aryl, heteroaryl, alkylaryl, alkylheteroaryl, arylalkyl, or heteroarylalkyl;
X is O, S, NH, $CR_{11}R_{12}$, or $NR_{13}$, wherein $R_{11}$-$R_{13}$ are independently hydrogen, substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl;
Y is O or S;
when X and Y are O, the indeterminate bond is a double bond, $R_1$, $R_2$, $R_4$, $R_5$, $R_6$, and $R_{10}$ are H, and $R_3$, $R_7$, and $R_9$ are hydroxyl, then $R_8$ is not an alkenyl substituted with hydroxyl, OH—$CH_2$—, or carbonyl;
when X and Y are O, the indeterminate bond is a double bond, $R_2$, $R_4$, $R_5$, $R_6$, and $R_{10}$ are H, and $R_1$, $R_3$, $R_7$, and $R_9$ are hydroxyl, then $R_8$ is not an alkenyl substituted with hydroxyl or OH—$CH_2$—; and
the composition is a cosmetic composition.
2. The composition of claim 1, wherein X and Y are O; or
wherein the compound is polyphenol having at least three hydroxyl groups at positions selected from $R_1$-$R_7$ and $R_9$; or
wherein the alkenyl of the at least one of $R_8$ and $R_{10}$ is substituted with aryl or heteroaryl; or
wherein the alkenyl of the at least one of $R_8$ and $R_{10}$ is $C_2$-$C_{10}$ alkenyl; or
wherein $R_8$ is substituted alkenyl; or
wherein $R_8$ is substituted alkenyl and $R_{10}$ is hydrogen, $C_1$-$C_{10}$ alkyl, or $C_1$-$C_{10}$ alkyoxyl; or
wherein $R_1$, $R_2$, $R_3$, $R_4$, $R_5$, $R_6$, $R_7$, and $R_9$ are independently hydrogen, $C_1$-$C_{10}$ alkyl, or $C_1$-$C_{10}$ alkyoxyl.
3. The composition of claim 1, wherein the compound has the structure of Formula 2

Formula 2

4. The composition of claim 1, wherein the compound has the structure of Formula 3

Formula 3

5. The composition of claim 1, wherein the composition reduces melanin content, limits melanin distribution, induces autophagy of melanosome, or a combination thereof, in subjects to which the composition is administered; or
wherein the composition does not cause cytotoxicity in subjects to which the composition is administered; or
wherein the composition further comprises tomato extract, citrus extract, Herba Dendrobii extract, phenylalanine, or a mixture thereof; or
wherein the composition is effective in mitigating, preventing, treating, or a combination thereof, one or more skin conditions selected from the group consisting of solar lentigines, melasma, freckles, discoloration, post-inflammatory hyperpigmentation, and a combination thereof, in subjects to which the composition is administered.

6. A method of lightening skin, reducing hyperpigmentation, or both in an area of a skin of a subject, comprising administering to the subject a composition according to claim 1.

7. The method of claim 6, wherein the administration of the composition reduces the synthesis of melanin in the subject, reduces the amount of melanin in the subject, limits the distribution of melanin in the subject, or a combination thereof; or
wherein the administration of the composition inhibits or reduces an activity, the expression, or an activity and the expression of tyrosinase, tyrosinase-related protein 1, tyrosinase-related protein 2, or a combination thereof; or
wherein the administration of the composition induces autophagy of melanosomes in the subject; or
wherein the administration of the composition does not cause cytotoxicity in the subject; or
wherein the composition is administered by topical application to body surface, injection to the dermal tissue, implantation under skin, of a combination thereof; or
wherein the composition further comprises tomato extract, citrus extract, Herba Dendrobii extract, phenylalanine, or a mixture thereof; or
wherein the administration of the composition is effective in mitigating, preventing, treating, or a combination thereof, one or more skin conditions selected from the group consisting of solar lentigines, melasma, freckles, discoloration, post-inflammatory hyperpigmentation, and combinations thereof.

8. A method of (1) safely and effectively lightening skin tone, reducing hyperpigmentation, or both, (2) suppressing melanogenesis and accelerating the reduction of synthesized melanin, or (3) lightening skin, depigmenting skin, or both, through inhibiting the synthesis of melanin and inducing the autophagy of melanosome, comprising administering to the subject a composition according to claim 1.

9. The composition of claim 1 further comprising one or more additives selected from the group consisting of urea, guanidine, glycerol, petrolatum, mineral oil, sugar esters and polyesters, polyolefins, methyl isostearate, ethyl isostearate, cetyl ricinoleate, isononyl isononanoate, isohexadecane, lanolin, lanolin esters, cholesterol, pyrrolidone carboxylic acid/salt (PCA), trimethyl glycine (betaine), tranexamic acid, amino acids and their salts, panthenol and its derivatives, collagen, hyaluronic acid, elastin, hydrolysates, primrose oil, jojoba oil, epidermal growth factor, soybean saponins, and mucopolysaccharides.

10. The composition of claim 1 in a form selected from the group consisting of a skin lotion, cream, gel, emulsion, spray, conditioner, cosmetic, lipstick, foundation, and nail polish.

11. A composition comprising
(a) a compound having the structure of Formula 1

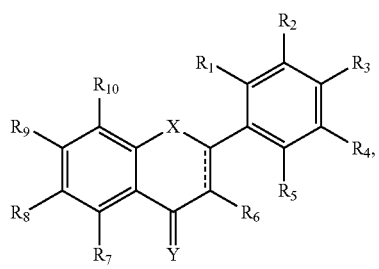

Formula 1 stereoisomeric form thereof, tautomeric form thereof, a pharmaceutically acceptable salt thereof, a pharmaceutically acceptable solvate thereof, a pharmaceutically acceptable polymorph thereof, or a prodrug thereof; and
(b) a pharmaceutically acceptable excipient;
wherein
$R_1$-$R_{10}$ are independently hydrogen, halogen, hydroxyl, or substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl;
at least one of $R_8$ and $R_{10}$ is alkenyl substituted with aryl, heteroaryl, alkylaryl, alkylheteroaryl, arylalkyl, or heteroarylalkyl;
X is O, S, NH, $CR_{11}R_{12}$, or $NR_{13}$, wherein $R_{11}$-$R_{13}$ are independently hydrogen, substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl;
Y is O or S, and
the composition is a cosmetic composition.

12. The composition of claim 1, wherein one of $R_8$ and $R_{10}$ is hydrogen, $C_1$-$C_{10}$ alkyl, or $C_1$-$C_{10}$ alkyoxyl.

13. A composition comprising
(a) a compound having the structure of Formula 1

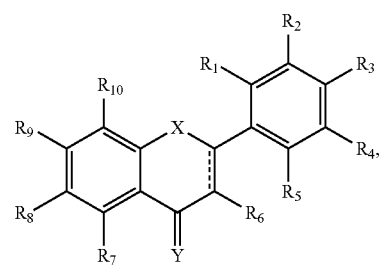

Formula 1 stereoisomeric form thereof, tautomeric form thereof, a pharmaceutically acceptable salt thereof, a pharmaceutically acceptable solvate thereof, a pharmaceutically acceptable polymorph thereof, or a prodrug thereof; and
(b) a pharmaceutically acceptable excipient;
wherein
X and Y are independently O or S;
$R_8$ and $R_{10}$ are independently hydrogen, halogen, hydroxyl, or substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl;
at least one of $R_8$ and $R_{10}$ is alkenyl substituted with aryl, heteroaryl, alkylaryl, alkylheteroaryl, arylalkyl, or heteroarylalkyl;
$R_1$-$R_7$ and $R_9$ are independently hydrogen, $C_1$-$C_{10}$ alkyl, $C_1$-$C_{10}$ alkyoxyl, or hydroxyl group; and
the composition is a cosmetic composition.

14. The composition of claim 13, wherein at least one of $R_8$ and $R_{10}$ is alkenyl substituted with aryl or heteroaryl.

15. The composition of claim 13, wherein at least three of $R_1$-$R_7$ and $R_9$ are hydroxyl groups.

16. The composition of claim 1, wherein the compound is in an amount between 1 μM and 10 mM, or between 1 μM and 1 mM, or between 10 μM and 200 μM.

17. The composition of claim 1, wherein the compound is in an amount equal to or lower than 20 μM.

18. A composition comprising
(a) a compound having the structure of Formula 1

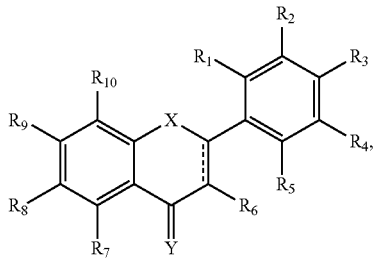

Formula 1 stereoisomeric form thereof, tautomeric form thereof, a pharmaceutically acceptable salt thereof, a pharmaceutically acceptable solvate thereof, a pharmaceutically acceptable polymorph thereof, or a prodrug thereof; and
(b) a pharmaceutically acceptable excipient;
wherein
$R_1$-$R_{10}$ are independently hydrogen, halogen, hydroxyl, or substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl;
for $R_1$-$R_{10}$ the substituted alkenyl is independently arylalkenyl or heteroarylalkenyl;
X is O, S, NH, $CR_{11}R_{12}$, or $NR_{13}$, wherein $R_{11}$-$R_{13}$ are independently hydrogen, substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl;
Y is O or S; and
the composition is a cosmetic composition.

19. A composition comprising
(a) a compound having the structure of Formula 1

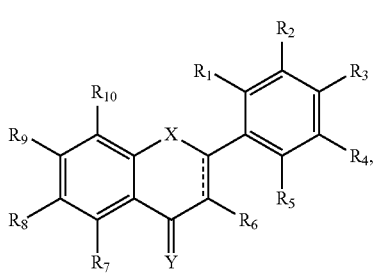

Formula 1 stereoisomeric form thereof, tautomeric form thereof, a pharmaceutically acceptable salt thereof, a pharmaceutically acceptable solvate thereof, a pharmaceutically acceptable polymorph thereof, or a prodrug thereof; and
(b) a pharmaceutically acceptable excipient;
wherein
$R_1$-$R_{10}$ are independently hydrogen, halogen, hydroxyl, or substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl;
for $R_1$-$R_{10}$ the substituted alkenyl is independently styryl;
X is O, S, NH, $CR_{11}R_{12}$, or $NR_{13}$, wherein $R_{11}$-$R_{13}$ are independently hydrogen, substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl;
Y is O or S; and
the composition is a cosmetic composition.

20. A composition comprising
(a) a compound having the structure of Formula 1

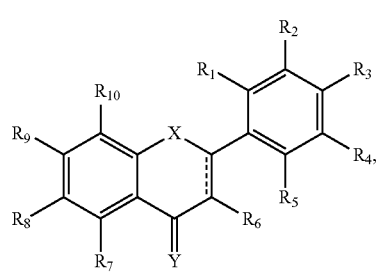

Formula 1 stereoisomeric form thereof, tautomeric form thereof, a pharmaceutically acceptable salt thereof, a pharmaceutically acceptable solvate thereof, a pharmaceutically acceptable polymorph thereof, or a prodrug thereof; and
(b) a pharmaceutically acceptable excipient;
wherein
$R_1$-$R_{10}$ are independently hydrogen, halogen, hydroxyl, or substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl;
at least one of $R_8$ and $R_{10}$ is styryl;
X is O, S, NH, $CR_{11}R_{12}$, or $NR_{13}$, wherein $R_{11}$-$R_{13}$ are independently hydrogen, substituted or unsubstituted alkyl, heteroalkyl, alkenyl, heteroalkenyl, alkynyl, heteroalkynyl, cycloalkyl, heterocycloalkyl, cycloalkenyl, heterocycloalkenyl, aryl, heteroaryl, alkylaryl, alkylheteroaryl, arylalkyl, or heteroarylalkyl;
Y is O or S; and
the composition is a cosmetic composition.

* * * * *